US012297287B2

(12) United States Patent
Redlich

(10) Patent No.: US 12,297,287 B2
(45) Date of Patent: May 13, 2025

(54) CD14 ANTAGONIST ANTIBODIES FOR TREATING NEURODEGENERATIVE DISEASES

(71) Applicant: Implicit Bioscience Limited, Woolloongabba (AU)

(72) Inventor: Garry Llewellyn Redlich, East Brisbane (AU)

(73) Assignee: IMPLICIT BIOSCIENCE LIMITED, Queensland (AU)

( * ) Notice: Subject to any disclaimer, the term of this patent is extended or adjusted under 35 U.S.C. 154(b) by 599 days.

(21) Appl. No.: 17/483,517

(22) Filed: Sep. 23, 2021

(65) Prior Publication Data

US 2022/0010025 A1     Jan. 13, 2022

Related U.S. Application Data

(63) Continuation of application No. 16/606,727, filed as application No. PCT/AU2018/050357 on Apr. 20, 2018, now abandoned.

(30) Foreign Application Priority Data

Apr. 21, 2017 (AU) ................................ 2017901462
Mar. 8, 2018 (AU) ................................ 2018900762

(51) Int. Cl.
| | | |
|---|---|---|
| *C07K 16/28* | (2006.01) |
| *A61K 38/00* | (2006.01) |
| *A61K 45/06* | (2006.01) |
| *A61P 25/02* | (2006.01) |
| *A61P 25/28* | (2006.01) |

(52) U.S. Cl.
CPC .......... *C07K 16/2896* (2013.01); *A61P 25/02* (2018.01); *A61P 25/28* (2018.01); *A61K 38/00* (2013.01); *A61K 45/06* (2013.01); *C07K 2317/24* (2013.01); *C07K 2317/51* (2013.01); *C07K 2317/515* (2013.01); *C07K 2317/565* (2013.01); *C07K 2317/70* (2013.01)

(58) Field of Classification Search
CPC ............ C07K 16/2896; C07K 2317/24; C07K 2317/51; C07K 2317/515; C07K 2317/565; C07K 2317/70; A61P 25/02; A61P 25/28; A61K 38/00; A61K 45/06; A61K 2039/545; A61K 2039/505
See application file for complete search history.

(56) References Cited

U.S. PATENT DOCUMENTS

| | | | |
|---|---|---|---|
| 5,820,858 A | 10/1998 | Leturcq |
| 6,444,206 B1 | 9/2002 | Leturcq |
| 7,326,569 B2 | 2/2008 | Leturcq |
| 2004/0091478 A1 | 5/2004 | Furusako |
| 2006/0121574 A1 | 6/2006 | Allison |

FOREIGN PATENT DOCUMENTS

| | | |
|---|---|---|
| KR | 20100101467 A | 9/2010 |
| WO | 9101639 A1 | 2/1991 |
| WO | 9428025 A1 | 12/1994 |
| WO | 9608272 A1 | 3/1996 |
| WO | 0242333 A1 | 5/2002 |
| WO | 2006/063292 | 6/2006 |
| WO | 2018/165720 | 9/2018 |
| WO | 2019/217916 | 11/2019 |

OTHER PUBLICATIONS

Adachi et al., "Inhibition by a CD14 monoclonal antibody of lipopolysaccharide binding to murine macrophages," J. Endotoxin Res. (1999) 5:139-146.
Alexianu et al. "Immune Reactivity in a Mouse Model of Familial ALS Correlates With Disease Progression," Neurology (2001) 57(7): 1282-1289.
Altschul, S.F. et al. (1997). "Gapped BLAST and PSI-BLAST: A New Generation of Protein Database Search Programs," Nucleic Acids Res. 25(17):3389-3402.
Axtelle et al., IC14, a CD14 Specific Monoclonal Antibody, Is a Potential Treatment for Patients With Severe Sepsis, J Endotoxin Res (2001) 7(4): 310-314.
Bazil et al., "Biochemical Characterization of a Soluble Form of the 53-kDa Monocyte Surface Antigen," Eur J Immunol (1986) 16(12): 1583-1589.
Bird et al. "Single-Chain Antigen-Binding Proteins," Science (1988) 242: 423-426.
Butovsky et al., "Modulating Inflammatory Monocytes With a Unique microRNA Gene Signature Ameliorates Murine ALS," J Clin Invest (2012) 122(9): 3063-3087.
Carter, P. et al. (May 1992). "Humanization of an Anti-p185HER2 Antibody for Human Cancer Therapy," Proc. Natl. Acad. Sci. USA 89:4285-4289.
Chothia et al., "Structural Repertoire of the Human VH Segments," J Mol Biol (1992) 227(3): 799-817.
Chothia, C. et al. (1987), "Canonical Structures for the Hypervariable Regions of Immunoglobulins," J. Mol. Biol, 196:901-917.
Chothia, C. et al. (Dec. 1989). "Conformations of Immunoglobulin Hypervariable Regions," Nature 342 (6252):877-883.
Corcia et al., "Molecular Imaging of Microglial Activation in Amyotrophic Lateral Sclerosis," PLoS One (2012) 7(12) e52941.

(Continued)

*Primary Examiner* — Olga N Chernyshev
(74) *Attorney, Agent, or Firm* — Morrison & Foerster LLP

(57) ABSTRACT

This invention relates generally to agents and methods for treating the development or progression of a neurodegenerative disease. In particular, the present invention relates to CD14 antagonists for use in treating the development or progression of a neurodegenerative disease, including Motor Neurone Disease (MND) and Dementia disease or associated symptoms. The present invention further provides compositions including such agents.

6 Claims, 3 Drawing Sheets

Specification includes a Sequence Listing.

(56) References Cited

OTHER PUBLICATIONS

Deveraux et al., "A comprehensive set of sequence analysis programs for the VAX," Nucleic Acids Res (1984) 12(1 Pt 1):387-395.
Fassbender et al., "The LPS receptor (CD14) links innate immunity with Alzheimer's disease," FASEB J (2004) 18 (1): 203-205 Published Online 2003.
Fiala et al., "IL-17A Is Increased in the Serum and in Spinal Cord CD8 and Mast Cells of ALS Patients," J Neuroinflammation (2010) 7: 76.
Fiala et al., "Tocilizumab Infusion Therapy Normalizes Inflammation in Sporadic ALS Patients," Am J Neurodegener Dis (2013) 2(2): 129-139.
Foote, J. et al. (1992). "Antibody Framework Residues Affecting the Conformation of the Hypervariable Loops," J Mol Biol. 224(2): 487-499.
Guillemin et al., "Obtention and Characterization of Primary Astrocyte and Microglial Cultures From Adult Monkey Brains," J Neurosci Res (1997) 49(5): 576-591.
Henkel et al., "The Chemokine MCP-1 and the Dendritic and Myeloid Cells It Attracts are Increased in the mSOD1 Mouse Model of ALS," Mol Cell Neurosci (2006) 31(3): 427-437.
Huston, J.R. et al. (Aug. 1988). "Protein Engineering of Antibody Binding Sites: Recovery of Specific Activity in an Anti-Digoxin Single-Chain Fv Analogue Produced in *Escherichia coli*," Proc. Natl. Acad. Sci. U.S.A. 85(16)5879-5883.
Illarregui et al., "New Roles for CD14 and IL-β Linking Inflammatory Dendritic Cells to IL-17 Production in Memory CD4+ T Cells," Immunol Cell Biol (2016) 94(10): 907-916.
Jersmann, H. "Time to Abandon Dogma: CD14 Is Expressed by Non-Myeloid Lineage Cells," Immunol Cell Biol (2005) 83(5): 462-467.
Jones, P.T. et al. (May 29, 1986). "Replacing the Complementarity-Determining Regions in a Human Antibody With Those From a Mouse," Nature 321:522-525.
Juan et al., "Identification of a Domain in Soluble CD14 Essential for Lipopolysaccharide (LPS) Signaling but Not LPS Binding," J Biol Chem (1995) 270(29): 17237-17242.
Juan et al., "Identification of a Lipopolysaccharide Binding Domain in CD14 Between Amino Acids 57 and 64," J Biol Chem (1995) 270(10): 5219-5224.
Kabat, E. A. et al., "Sequences of Proteins of Immunological Interest," Fifth Edition, U.S. Department of Health and Human Services, NIH Publication No. 91-3242 (1991), 83 pages.
Kiernan et al., "Amyotrophic Lateral Sclerosis," Lancet (2011) 377(9769): 942-955.
Lee et al., "Pharmacological Inhibition of Complement C5a-C5a 1 Receptor Signalling Ameliorates Disease Pathology in the hSOD1 G93A Mouse Model of Amyotrophic Lateral Sclerosis," Br J Pharmacol (2017) 174(8): 689-699.
Leturcq et al., "Antibodies Against CD14 Protect Primates From Endotoxin-Induced Shock," J Clin Invest (1996) 98 (7): 1533-1538.
MacCallum et al., "Antibody-antigen interactions: Contact analysis and binding site topography," J. Mol. Biol. (1996) 262, 732-745.
Meissner et al., "Mutant Superoxide Dismutase 1-induced IL-1beta Accelerates ALS Pathogenesis," Proc Natl Acad Sci U S A (2010) 107(29): 13046-13050.
Murdock et al., "Increased Ratio of Circulating Neutrophils to Monocytes in Amyotrophic Lateral Sclerosis," Neurol Neuroimmunol Neuroinflamm (2016) 3(4): e242.
Padlan, E.A. et al. (Jan. 1995). "Identification of Specificity-Determining Residues in Antibodies," FASEB J. 9 (1):133-139.
Pase et al., "Association of CD14 with incident dementia and markers of brain aging and injury," Neurology (2020) 94 (3):e254-e266.
Presta, "Antibody engineering," Curr Opi Struct Biol (1992) 2(4):593-596.
Ransohoff et al., "Multiple Sclerosis—A Quiet Revolution," Nat Rev Neurol (2015) 11(3): 134-142.
Reed-Geaghan et al., Deletion of CD14 Attenuates Alzheimer's Disease Pathology by Influencing the Brain's Inflammatory Milieu, 2010, 30(46), The Journal of Neuroscience.
Rentzos et al., "Interleukin-17 and interleukin-23 are Elevated in Serum and Cerebrospinal Fluid of Patients With ALS: A Reflection of Th17 Cells Activation?" Acta Neurol Scand (2010) 122(6): 425-429.
Riechmann, L. et al. (Mar. 1988). "Reshaping Human Antibodies for Therapy," Nature 332:323-329.
Salter et al., "Microglia Emerge as Central Players in Brain Disease," Nat Med (2017) 23(9): 1018-1027.
Sambrook et al., Molecular Cloning. A Laboratory Manual (Cold Spring Harbor Press 1989) at sections 1.101 to 1.104.
Sandhu, "Protein Engineering of Antibodies," Crit Rev Biotechnol (1992) 12(5-6): 437-462.
Singer et al., "Optimal Humanization of 1B4, an anti-CD18 Murine Monoclonal Antibody, Is Achieved by Correct Choice of Human V-region Framework Sequences," J Immunol (1993) 150(7): 2844-2857.
Supplementary European Search Report for EP 18788123.0, mailed Jan. 28, 2021, 12 pages.
Tasaka et al., "Effect of CD14 Blockade on Endotoxin-Induced Acute Lung Injury in Mice," Am J Respir Cell Mol Biol (2003) 29(2): 252-258.
Tato et al., "SnapShot: Cytokines I," Cell (2008) 132(2): 324.
Tato et al., "SnapShot: Cytokines II," Cell (2008) 132 (3): 500.
Tato et al., "SnapShot: Cytokines III," Cell (2008) 132(5): 900.
Tempest et al., "Reshaping a Human Monoclonal Antibody to Inhibit Human Respiratory Syncytial Virus Infection in Vivo," Biotechnology (N Y) (1991) 9(3): 266-271.
Turner et al., "Evidence of Widespread Cerebral Microglial Activation in Amyotrophic Lateral Sclerosis: An [11C](R)-PK11195 Positron Emission Tomography Study," Neurobiol Dis (2004) 15(3): 601-609.
Van Der Meer et al., "Blocking IL-1beta to Slow Down Progression of ALS?" Proc Natl Acad Sci U S A (2010) 107 (29): 12741-12742.
Van Voorhis et al., "Specific Antimononuclear Phagocyte Monoclonal Antibodies. Application to the Purification of Dendritic Cells and the Tissue Localization of Macrophages," J Exp Med (1983) 158(1): 126-145.
Venegas et al., "Danger-associated Molecular Patterns in Alzheimer's Disease," J Leukoc Biol (2017) 101(1): 87-98.
Verhoeyen et al., "Reshaping human antibodies: grafting an antilysozyme activity," Science (1988) 239 (4847):1534-1536.
Ward et al. "Binding Activities of a Repertoire of Single Immunoglobulin Variable Domains Secreted From *Escherichia coli*," Nature (1989) 341:544-546.
Zhao et al., "Extracellular Mutant SOD1 Induces Microglial-Mediated Motoneuron Injury," Glia (2010) 58(2): 231-243.
Zhao et al., "TDP-43 Activates Microglia Through NF-κB and NLRP3 Inflammasome," Exp Neurol (2015) 273: 24-35.
Appel et al., "The microglial-motoneuron dialogue in ALS," Acta Myol. (2011) 30(1):4-8.
Spek et al., "Treatment with an anti-CD14 monoclonal antibody delays and inhibits lipopolysaccharide-induced gene expression in humans in vivo," J Clin Immunol. (2003) 23(2):132-140.
Cao et al., "The contributing role of CD14 in toll-like receptor 4 dependent neuropathic pain," Neuroscience (2009) 158(2):896-903.
Henderson et al., "Phase 1b dose-escalation, safety, and pharmacokinetic study of IC14, a monoclonal antibody against CD14, for the treatment of amyotrophic lateral sclerosis," Medicine (2021) 100:42(e27421).
Neves et al., "Antibody Approaches to Treat Brain Diseases," Trends in Biotechnology (2016) 34(1):36-48.
Verbon et al., "Effects of IC14, an Anti-CD14 Antibody, on Coagulation and Fibrinolysis during Low-Grade Endotoxemia in Humans," JID 187:55-61.

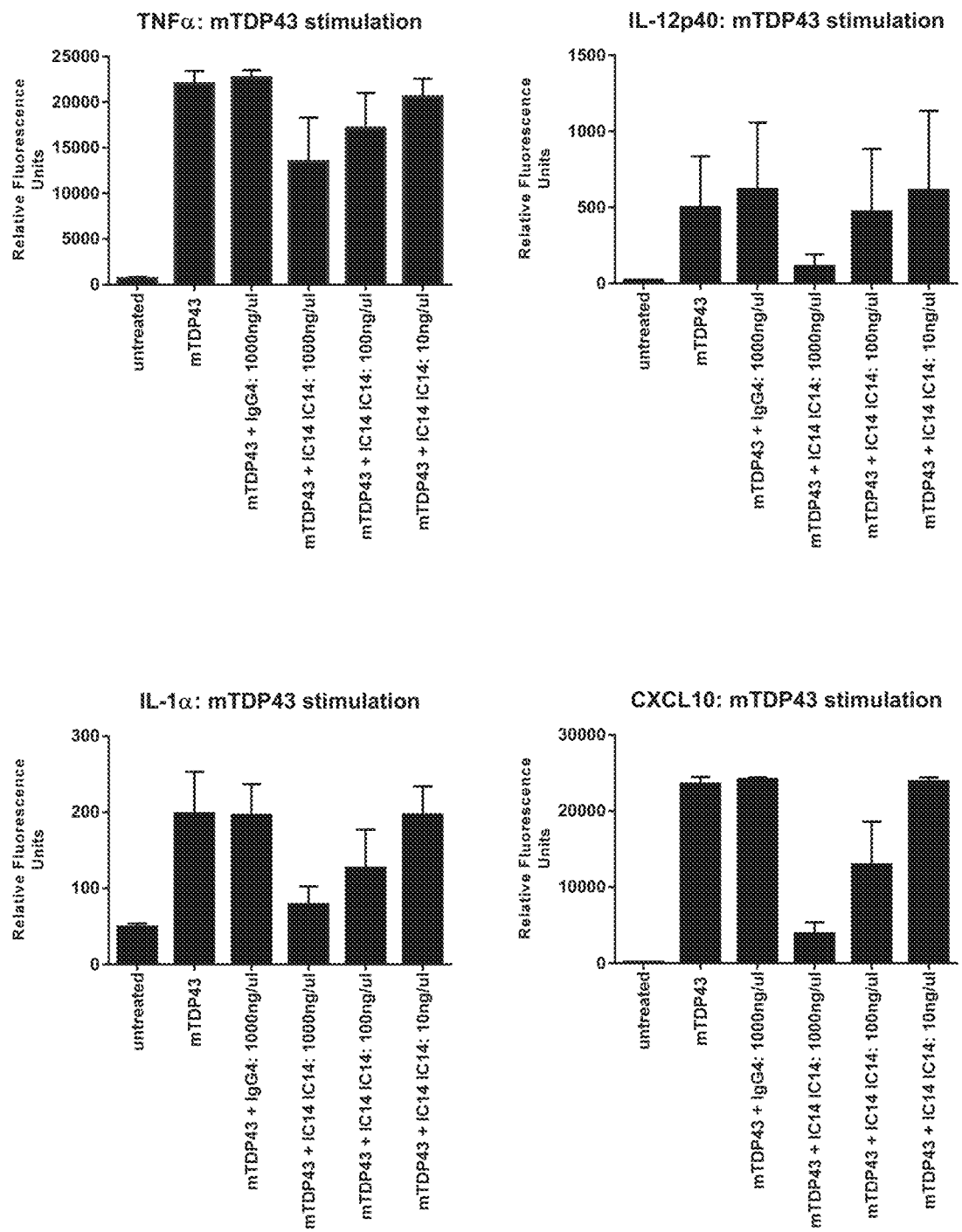

CD14 ANTAGONIST ANTIBODIES FOR TREATING NEURODEGENERATIVE DISEASES

RELATED APPLICATIONS

This application is a continuation of U.S. patent application Ser. No. 16/606,727, filed Oct. 18, 2019, which is a U.S. national phase of PCT application PCT/AU2018/050357 having an international filing date of 20 Apr. 2018, which claims benefit of Australian Provisional Application No. 2017901462 entitled "Agents for treating or preventing motor neurone disease and uses therefor" filed 21 Apr. 2017 and Australian Provisional Application No. 2018900762 entitled "Agents for treating disease and uses therefor" filed 8 Mar. 2018, the contents of which are incorporated herein by reference in their entirety.

The present application is being filed along with a Sequence Listing in electronic format. The Sequence Listing is provided as a file entitled 229752007601SeqList.TXT, created Sep. 23, 2021, which is 16,378 bytes in size. The information in the electronic format of the Sequence Listing is incorporated by reference in its entirety.

FIELD OF THE INVENTION

This invention relates generally to agents and methods for treating the development or progression of a neurodegenerative disease. In particular, the present invention relates to CD14 antagonists for use in treating the development or progression of a neurodegenerative disease, including Motor Neurone Disease (MND) and Dementia disease or associated symptoms. The present invention further provides compositions including such agents.

BACKGROUND OF THE INVENTION

Neurodegenerative diseases are highly debilitating conditions characterized by a progressive loss of structure and function of neurons, ultimately leading to death of neurons, which have an adverse impact on the quality of life and ultimately lead to early death. There is also a significant social impact on surrounding family members and the community. As the population becomes older, the palliative care required for patients suffering from neurodegenerative disorders is becoming a significant health cost to the community. In the United States alone, management of neurodegenerative disease patients and lost productivity is in the tens of billions of dollars annually. The ALS Therapy Development Institute in Cambridge, Massachusetts, estimates the number of Motor Neurone Disease (MND) patients at more than 30,000 in the US and at least 450,000 worldwide. In 2010 the global cost of dementia was estimated to be $604 billion, approximately 1% of the worlds gross domestic product, whilst in the USA the Alzheimer's Association estimates the cost of care for Alzheimer's disease (AD) patients at $200 billion/year. If present trends continue, this cost is projected to grow to $1.1 trillion per year by 2050. Whilst significant research to find cures for these debilitating conditions is ongoing, it is likely to be decades before successful treatments to reverse or prevent the effects of neurodegeneration are found.

The most common neurodegenerative diseases include MND, e.g. Amyotrophic lateral sclerosis (ALS), Primary lateral sclerosis (PLS), Progressive muscular atrophy (PMA), Progressive bulbar palsy (PBP) and Pseudobulbar palsy, and Dementia (e.g. Alzheimer's disease, the Lewy body dementias—dementia with Lewy bodies (DLB) and Parkinson's Disease Dementia (PDD), Vascular Dementia and Frontotemporal dementia (FTD)), Parkinson's disease and Huntington's disease.

Motor neurone disease (MND) is a devastating progressive disease that typically leads to death within 4-6 years of onset. The incidence of MND is fairly uniform at 2-3 cases per 100,000 person-years, with a peak age at onset of 58-63 years for sporadic disease and 47-52 years for familial disease (Kiernan M. C., et al. Lancet 377:942-955 (2011)). Pathologically, MND is characterized by the loss of motor neurones in the motor cortex, brainstem and spinal cord. Patients typically present with progressive muscle atrophy, paralysis, spasticity, and hyperreflexia and this ultimately leads to death through failure of the respiratory muscles (Zhao W., et al. Glia 58:231-243 (2010)). Treatment options for MND are severely limited. Although numerous therapies have demonstrated efficacy in rodent models and appeared efficacious in small-scale phase 2 clinical trials, only two compounds, riluzole (Rilutek®/Teglutik®) and edaravone (Radicava®/Radicut®), have received US Food and Drug Administration (FDA) approval in the last 23 years. Both have limited efficacy, extending patient survival for 3-4 months without improving quality of life. Another drug currently in phase III trials is Genervon's drug candidate GM604 which is an endogenous embryonic stage tyrosine kinase motoneuronotrophic factor regulator which binds to the insulin receptors, IGF1 receptors, and IGF2 of the human nervous system. Despite showing several positive effects in relation to amyotrophic lateral sclerosis (ALS) symptoms in clinical trials (the most common form of MND), in the company's own words, the drug does not itself present a "cure". The uniform failure of a curative ALS trial and 99.6% failure rate of AD trials are a testimony that the pervasive and dominating drug development paradigm of single/gene target reductionism cannot cure ALS and other neurological and neurodegenerative multifactorial diseases. This means that there is considerable room for improvement in therapeutic development of treatment for neurodegenerative disease and symptoms thereof and emphasizes the unmet medical need.

ALS accounts for approximately 60-70% of all MND cases. In the USA, ALS is generally known as 'Lou Gehrig's disease' and affects about 7 in every 100,000 people. There are two forms of ALS, familial where subjects exhibit an inherited mutation in a gene and sporadic. Genes with mutations linked to ALS (and other forms of MND) include C9ORF72, the most common genetic cause of ALS, Cu/Zn superoxide dismutase (SOD1), NEK1, TAR DNA binding protein 43 (TDP-43), Fused in sarcoma (FUS) and Ubiquilin-2 (UBQLN2). Mutations in the genes including VCP (valosin-containing protein), ALS2 (alsin), SETX (senataxin), ANG (angiogenin), PFN1 (profilin-1), MATR3 (matrin-3), CHCHD10 (coiled-coil-helix-coiled-coil-helix domain containing 10), TUBA4A (tubulin, alpha 4A), TBK1 (TANK-binding kinase 1), C21orf2 and OPTN (optineurin) are also found in a small percentage of patients.

The causative nature of ALS is varied and in this regard the disease can be considered as a spectrum disorder. ALS is characterized by rapidly progressive muscle atrophy, dysarthria and dyspnea. The disconnect between muscle and neurons leads to respiratory failure after about 40 months. There is degeneration of the upper and lower motor neurones leading to muscle weakening and atrophy due to inability for the muscles to function. Ultimately, there is complete debilitation. Whilst generally cognitive function is spared, the muscle atrophy is sufficient to significantly reduce a patient's quality of life.

In recent years there has been a growing appreciation of the importance of inflammation in the progression of neurological diseases. The role of inflammation in neuronal disease has long been recognized in multiple sclerosis, resulting in the introduction of immunomodulatory drugs which have had significant therapeutic impact (Ransohoff, R. M., et al. Nat. Rev. Neurol. 11, 134-142 (2015)).

Immune responses in the brain and spinal cord are primarily mediated by microglia, the brain's resident immune cells. By responding to activation by pathological changes in the central nervous system (CNS), for example, the release of danger signals such as damage-associated molecular patterns (DAMPs) from damaged tissues, they act as a first line of defense and play a key role in initiating the production of pro-inflammatory mediators and in sustaining neuroinflammatory responses. Studies have shown microglial activation at the site of motor neurone damage in both MND patients and in murine MND models, with widespread microglial activation detectable by PET scan in the brains of living MND patients (Turner M. R., et al. Neurobiol. Dis. 15:601-9 (2004); Corcia P., et al. PLoS One 7:6-12 (2012)). A correlation has also been demonstrated between the severity of upper motor neurone signs in MND patients and levels of microglial activation in the motor cortex (Turner M. R., et al. Neurobiol. Dis. 15:601-9 (2004)). Mouse MND models have also supported a role for microglia in disease progression, indicating MND-activated microglia precede disease onset and increase with disease progression through end-stage disease (Henkel J. S. et al. Mol. Cell. Neurosci. 31:427-37 (2006); Alexianu M. E. et al, Neurology 57:1282-9 (2001)), with the intensity of microglial activation paralleling the motor neurone degeneration and supporting an active role for microglia.

A number of DAMPs have been identified in the brain of Alzheimer's patients. These include HMGB1, the S100 family members S100A9 and S100B, chromogranin, circulating DNA and the heat shock proteins (HSPs). With the exception of the HSPs all of these DAMPs have been shown to be elevated in disease, are physically associated with Aβ plaques and have been implicated in ongoing neuroinflammation (Venegas, C. & Heneka, M. T. 3. Leukoc. Biol. 101, 87-98 (2017)). The stimulation of microglia with Aβ results in the initiation of a number of pro-inflammatory responses, including cytokine and chemokine production.

Microglial activation has also been associated with neurodegeneration in Frontotemporal Dementia (FTD) and the Lewy body dementias (LBD) which include two closely related conditions, dementia with Lewy bodies (DLB) and Parkinson's disease dementia (PDD) which are the second most frequent cause of dementia in elderly adults. These degenerative brain diseases are associated with abnormal clumps of a protein called α-synuclein. FTD is a group of related conditions resulting from the progressive degeneration of the temporal and frontal lobes of the brain and is characterized by TDP-43 deposition. These areas of the brain play a significant role in decision-making, behavioral control, emotion and language. Both α-synuclein and TDP-43 may be acting as DAMPs. Microglial activation has also been associated with dopaminergic loss early in Parkinson's disease. This microglial activation also correlates inversely with cognitive function, suggesting that it may be related to disease pathology.

The diagnosis and therapy of diseases of the central nervous system could benefit from the application of highly specific monoclonal antibodies as drugs. However, one of the difficulties in developing treatments for neurodegenerative disorders is the issue of delivery of drugs to the target site across the blood brain barrier (BBB) into the CNS. This limits the efficiency of drugs targeted to brain diseases and makes it challenging to use biologic medicines for diseases of the brain. Because the size of even small antibody fragments (Fv, Fab) severely limits attempts to increase the delivery by passive diffusion through the intact BBB, methods that are under evaluation try either to circumvent the barrier by direct administration into cerebrospinal fluid or brain tissue, or to disrupt the barrier temporarily by hyperosmotic solutions. Both approaches require invasive techniques.

In view of the severity of neurodegenerative diseases, and the limited treatment options available, there is a need for agents and methods for treating neurodegenerative diseases.

SUMMARY OF THE INVENTION

The present invention arises in part from the determination that systemic administration of a CD14 antagonist antibody outside the central nervous system (CNS) of a subject with ALS inhibits the production of pro-inflammatory mediators (e.g. cytokines) by cells in the periphery of the subject, resulting in attenuation of disease progression and/or amelioration of the symptoms of ALS in the CNS, thus addressing the causal signals involved in generating and sustaining the inflammatory process rather than treating derivative inflammatory effectors.

CD14 is a glycoprotein that exists both in soluble form (sCD14) and in cell membrane-bound form (mCD14) on the surface of various cells, including for example, immune cells such as macrophages, monocytes, Kupffer cells, neutrophils, dendritic cells and B cells, as well as endothelial cells and epithelial cells (Jersmann, H P A, 2005. *Immunol Cell Biol.* 83: 462-467).

CD14 is a key molecule involved in mediating cellular activation via the pattern recognition receptor (PRR) family, molecules involved in the recognition of danger signals derived from either pathogens (pathogen associated molecular patterns (PAMPs)) or as a consequence of endogenous tissue damage or stress (damage associated molecular patterns (DAMPs)) by Toll-like receptors (TLRs), and initiation of the subsequent inflammatory cascade. CD14 is also known as a receptor for lipopolysaccharide (LPS)—also known as endotoxin- of Gram-negative bacteria, an exemplary PAMP, which receives LPS from LPS binding protein (LBP) in blood to form a complex. LPS also binds to sCD14 and the resulting complex can induce mCD14-independent production of pro-inflammatory mediators, including pro-inflammatory cytokines. Culturing human CD4+CD45RO+ memory T cells with soluble CD14 has also been shown to be sufficient for the upregulation of retinoic acid-related orphan receptor-γ thymus and IL-17 production (Ilarregui J. M., et al. Immunol. Cell Biol. 94: (2016)).

In addition to LPS, a component of Gram-negative bacteria, CD14 also acts as a co-receptor for other PAMPs, including for example, peptidoglycan and lipoteichoic acids of Gram-positive bacteria, lipoarabinomannan of mycobacteria and viral envelope proteins. CD14 also recognizes host-derived DAMP ligands that are endogenous molecules released from stressed, damaged or dying cells as a result of tissue injury and inflammation associated with a wide range of inflammatory situations. DAMPs exert their activity through interactions with members of the TLR family, and CD14 has been described as being required in mediating the activity of a number of these, including SOD1, TDP-43, members of the heat shock protein family as well as HMGB1, S100A and a variety of misfolded proteins associated with neurodegenerative disorders.

Pro-inflammatory cells and cytokines correlating with disease severity are present in the circulation of patients with neurodegenerative diseases. Altered levels of inflammatory monocytes have been observed in the circulation of MND patients and in murine MND models (Butovsky O. et al. 3. Clin. Invest. 122:3063 (2012); Murdock B. J., et al. Neurol. Neuroimmunol. Neuroinflammation 3:e242 (2016)). Furthermore, a small-scale study involving the treatment of MND patients with intravenous tocilizumab, a humanized antibody to the IL-6R, demonstrated that IV dosing diminished serum inflammatory cytokine levels and attenuated disease progression in a subset of patients (Fiala M., et al. Am. J. Neurodegener. Dis. 2:129-139 (2013)). Therapies targeting the inflammatory response associated with MND pathology have been considered. However, these are in relation to targeting the IL-6 receptor which addresses effectors of inflammation rather than targeting the primary initiators which drive degeneration and disease. Due to the role of CD14 in initiating the inflammatory cascade and pro-inflammatory mediator production, both via mCD14, and directly via sCD14, it is proposed herein that inhibiting or decreasing the CD14 mediated inflammatory response will provide a more efficacious treatment for inflammation associated with neurodegenerative diseases by addressing the cause of inflammation rather than the effect.

As described herein, inhibiting or decreasing the production of pro-inflammatory mediators by cells located outside the CNS of patients with a neurodegenerative disease using a CD14 antagonist antibody can treat the development or progression of the disease or symptoms thereof, including in the CNS.

Accordingly, in one aspect, the present invention provides methods of inhibiting or decreasing the production of a pro-inflammatory mediator (e.g. a cytokine) in a mammalian cell present in the periphery of a subject with a neurodegenerative disease, or at risk of developing a neurodegenerative disease. In an embodiment, these methods comprise, consist or consist essentially of contacting a peripheral cell comprising mCD14 with an anti-CD14 antagonist antibody in an amount sufficient to inhibit or decrease the production of a pro-inflammatory mediator from the cell.

In another embodiment, the methods comprise, consist or consist essentially of contacting peripheral circulating sCD14 with an anti-CD14 antagonist antibody in an amount sufficient to inhibit or decrease the production of a pro-inflammatory mediator from a peripheral cell.

Suitably, the peripheral cell is an immune cell (e.g. a monocyte, macrophage, dendritic cell or T cell).

The pro-inflammatory mediator is typically a cytokine, for example, tumor necrosis factor-$\alpha$ (TNF-$\alpha$), interleukin-1 (IL-1)-$\alpha$, IL-6, IFN-$\gamma$, IFN-$\beta$, IL-1$\beta$, IL-8, IL-17, or IL-18.

In related aspects, the methods defined above are used for treating neurodegenerative disease-mediated symptoms. These methods generally comprise, consist or consist essentially of contacting a peripheral cell comprising mCD14, or circulating sCD14, with a CD14 antagonist antibody, suitably in an amount sufficient to inhibit or decrease the CD14 dependent production of pro-inflammatory mediators in peripheral cells, to thereby treat the symptoms. In specific embodiments, the disease is MND or Dementia. Suitably, when the disease is MND (e.g. ALS), the symptoms include, for example, progressive muscle atrophy, paralysis, spasticity, respiratory changes and hyperreflexia. In an embodiment, the disease is Dementia, and the symptoms include for example, memory loss, depression, impaired communication, poor judgment, disorientation, confusion, sleep disorders, movement symptoms, hallucinations, neuroleptic sensitivity, behavior changes and difficulty speaking, swallowing and walking.

Yet another aspect of the present invention provides methods for treating the development or progression of a neurodegenerative disease or a symptom thereof in a subject. These methods generally comprise, consist or consist essentially of systemically administering an effective amount of a CD14 antagonist antibody to the subject to thereby treat the development or progression of the neurodegenerative disease, or a symptom thereof in the subject. In some embodiments, the production of one or more pro-inflammatory mediators in a peripheral cell of the subject is inhibited or decreased. Suitably, the pro-inflammatory mediator is a cytokine.

In related aspects, the present invention provides the use of a CD14 antagonist antibody for inhibiting or decreasing the production of one or more pro-inflammatory mediator/s (e.g. cytokines) by peripheral cells in a subject with a neurodegenerative disease or at risk of developing or progressing a neurodegenerative disease, or for treating the development or progression of a neurodegenerative disease. In some embodiments, the CD14 antagonist is manufactured as a medicament for any one or more of those applications.

In some embodiments, the methods further comprise identifying that the subject has or is at risk of developing or progressing a neurodegenerative disease, suitably prior to administration of the CD14 antagonist antibody. In illustrative examples of this type, the methods comprise determining the presence of a marker of a neurodegenerative disease in a biological sample, that is suitably taken from the subject, illustrative examples of which include blood, serum, plasma, saliva, cerebrospinal fluid, urine, skin or other tissues, or fractions thereof), suitably prior to administration of the CD14 antagonist antibody.

In an embodiment, the disease is a MND and the marker is selected from one or more of e.g. SOD1, TDP-43, FUS, C9ORF72, ALS2, ALS4, ALS8, NEK1, UBQLN2, VCP, SETX, ANG, PFN1, MATR3, CHCHD10, TUBA4A, TBK1, C21orf2 and OPTN or an expression product thereof. In this embodiment, the presence of a marker of a neurodegenerative disease is suitably determined by detecting presence or overexpression of an expression product of a marker gene and/or presence of a mutation in a marker gene (e.g., SOD1, TDP-43, FUS, C9ORF72, ALS2, ALS4, ALS8, NEK1, UBQLN2, VCP, SETX, ANG, PFN1, MATR3, CHCHD10, TUBA4A, TBK1, C21orf2 and OPTN mRNA or polypeptide) in the biological sample. In some embodiments for MND, the presence of cytoplasmic deposition of TDP-43-positive inclusions and/or elevated serum and/or CSF levels of neurofilaments, may also be determined.

In another embodiment, the disease is Dementia including Alzheimer's disease, FTD the LBD's (DLB and PDD) and Vascular Dementia and the marker is selected from one or more of a mutation in the gene encoding amyloid precursor protein (APP) and presenilins 1 and 2, mutations in the $\epsilon$4, 2 and 3 alleles of the apolipoprotein E (APOE) gene (APOE-$\epsilon$4, APOE-$\epsilon$2, APOE-$\epsilon$3), mutations in Triggering receptor expressed on myeloid cells 2 (TREM2) gene, MAPT gene on chromosome 17 that makes the protein tau, GRN gene, also called the PGRN gene, on chromosome 17 that makes progranulin protein, TARDBP gene on chromosome 1 that produces trans-active response DNA-binding protein of 43-kDa molecular weight (TDP-43), VCP gene on chromosome 9 that codes for valosin-containing protein and the CHMP2B gene on chromosome 3 that expresses charged multivesicular body protein 2B (also known as chromatin modifying protein 2B). Elevated serum and/or CSF levels of α-synuclein, S100A9 and S100B, chromogranin, circulating DNA, heat shock proteins and amyloid may also be determined.

In other embodiments, subjects at risk for a neurodegenerative disease may also be identified by determining the presence of elevated levels of one or more of pro-inflammatory markers associated with disease, e.g. TNF-α, interleukin-1 (IL-1)-α, IL-6, IFN-γ, IFN-β, IL-1β, IL-8, IL-18, C-reactive protein (CRP), IL-17, chemokines, CD14+-high monocytes and inflammatory mediator mRNA transcripts in peripheral blood mononuclear cells (PBMC). In an embodiment, the disease is MND and the cytokine detected is selected from one or more of IL-6 or IL-17. In an embodiment, the disease is Dementia and the cytokine detected is selected from IL-1, IL-6 and TNF-α.

In preferred embodiments, the CD14 antagonist antibody is IC14, or an antigen-binding fragment thereof.

The CD14 antagonist antibody may be administered alone or in combination with one or more ancillary agents that treat the development or progression of neurodegenerative disease or symptoms thereof. Accordingly, in still another aspect, the present invention provides pharmaceutical compositions formulated for systemic administration, suitably for treating the development or progression of a neurodegenerative disease or symptom thereof. These compositions comprise, consist or consist essentially of a CD14 antagonist antibody, optionally together with a pharmaceutically acceptable carrier or diluent. In an embodiment, the composition further comprises an ancillary anti-neurodegenerative agent.

In a related aspect, the present invention provides methods for treating the development or progression of a neurodegenerative disease or symptom thereof in a subject. These methods generally comprise, consist or consist essentially of administering concurrently to the subject an effective amount of a CD14 antagonist antibody administered systemically and an effective amount of an ancillary anti-neurodegenerative agent, to thereby treat the development or progression of the neurodegenerative disease, or a symptom thereof in the subject. Suitably, the CD14 antagonist antibody and the ancillary anti-neurodegenerative agent are administered in synergistically effective amounts.

In a specific embodiment, the ancillary anti-neurodegenerative agent is an anti-inflammatory agent. In an embodiment, the disease is MND (e.g. ALS) and the ancillary anti-neurodegenerative agent is selected from riluzole (Rilutek®/Teglutik®), a complement pathway inhibitor (e.g. PMX205 or eculizumab), an agent that blocks the interaction between CD40 and CD40 ligand, including antibodies that bind specifically to CD40 and/or CD40 ligand (e.g., AT-1501), NurOwn stem cell therapy (BrainStorm Cell Therapeutics), GM604, edaravone (Radicava®/Radicut®), Masitinib, Memantine or Tirasemtiv. In an embodiment, the disease is a dementia such as LBD, AD or FTD and the ancillary anti-neurodegenerative agent is a cholinesterase inhibitor. In another embodiment, the disease is AD and the ancillary agent is an approved therapeutic selected from for example, Aricept, Razadyne, Namenda, Exelon and Namzaric.

In another related aspect, the present invention provides the use of a CD14 antagonist antibody and an ancillary anti-neurodegenerative agent for treating the development or progression of a neurodegenerative disease, or symptom thereof. In some embodiments, the CD14 antagonist antibody and the ancillary anti-neurodegenerative agent are manufactured as a medicament for systemic administration for this application. Suitably, the CD14 antagonist antibody and the ancillary anti-neurodegenerative agent are formulated for concurrent administration.

BRIEF DESCRIPTION OF THE DRAWINGS

Embodiments of the disclosure are described herein, by way of non-limiting example only, with reference to the following drawings.

FIGS. 2A-2B show[[s]] the results of an in vitro assay assessing the effect of IC14 on cytokine or chemokine levels following TDP-43 activation of primary human microglia. Primary human microglia were pretreated with IC14 or control IgG4 antibody for 2 hrs before cells were stimulated with (FIG. 2A) mutant TDP-43 (mTDP43) or (FIG. 2B) wild-type TDP-43 (wtTDP43) for 48 hrs. Supernatants were collected for multiplex cytokine analysis. Untreated cells received neither antibody nor TDP-43, and reflect basal levels of cytokine or chemokine production. Expression was measured as Relative Fluorescence Units (RFU) and represents the average and SEM of three wells per sample.

DETAILED DESCRIPTION OF THE INVENTION

1. Definitions

Figure 1:
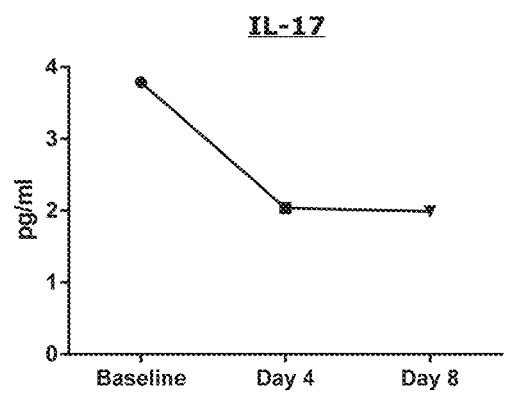
FIG. 1 shows the levels of IL-17, neurofilament light chain (NFL) and IL-18 in CSF after i.v. dosing of a MND patient with IC14 at a dosage of 4 mg/kg on Study Day 1 and 2 mg/kg on Study Days 2, 3 and 4.
Figure 1:
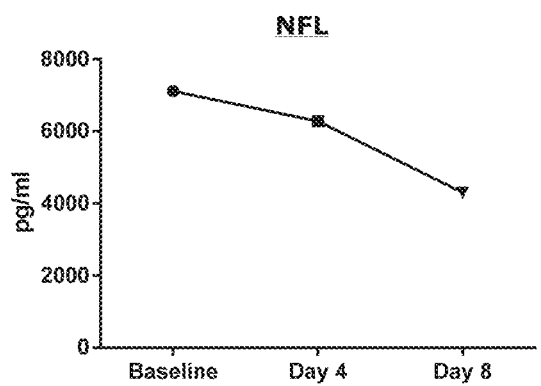
Figure 1:
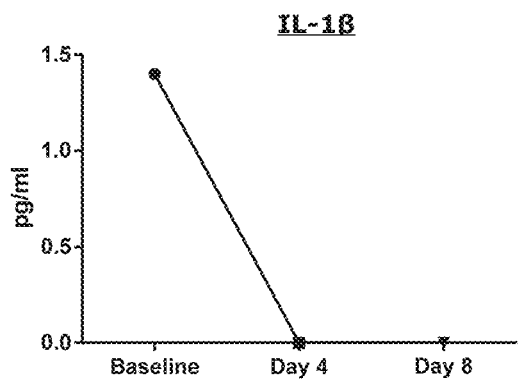

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e., to at least one) of the grammatical object of the article. By way of example, "an element" means one element or more than one element.

As used herein, "and/or" refers to and encompasses any and all possible combinations of one or more of the associated listed items, as well as the lack of combinations when interpreted in the alternative (or).

The terms "administration concurrently" or "administering concurrently" or "co-administering" and the like refer to the administration of a single composition containing two or more agents, or the administration of each agent as separate compositions and/or delivered by separate routes either contemporaneously or simultaneously or sequentially within a short enough period of time that the effective result is equivalent to that obtained when all such agents are administered as a single composition. By "simultaneously" is meant that the agents are administered at substantially the same time, and desirably together in the same formulation. By "contemporaneously" it is meant that the agents are administered closely in time, e.g., one agent is administered within from about one minute to within about one day before or after another. Any contemporaneous time is useful. However, it will often be the case that when not administered simultaneously, the agents will be administered within about one minute to within about eight hours and suitably within less than about one to about four hours. When administered contemporaneously, the agents are suitably administered at the same site on the subject. The term "same site" includes the exact location, but can be within about 0.5 to about 15 centimeters, preferably from within about 0.5 to about 5 centimeters. The term "separately" as used herein means that the agents are administered at an interval, for example at an interval of about a day to several weeks or months. The agents may be administered in either order. The term "sequentially" as used herein means that the agents are administered in sequence, for example at an interval or intervals of minutes, hours, days or weeks. If appropriate the agents may be administered in a regular repeating cycle.

The terms "ALS", "MND" and "Lou Gehrig's disease" may be used interchangeably herein to refer to the same condition. Both familial ALS and sporadic ALS may be treated or its development or progression delayed by the subject method. All forms of ALS are contemplated herein.

The term "agonist" refers to a ligand that stimulates a receptor to which it binds. An agonist, by classical definition, whether an orthosteric, allosteric, inverse or a co-agonist has a property to bind to a receptor, alter its receptor state and result in a biological action, including activation, whether directly or indirectly, of a chemical or physical signaling cascade, which results in a definable change in the behavior, physical or biological state of a cell. Consequently, agonism is defined as a property of an agonist to produce a biological action. In the context of the present invention, a CD14 agonist includes, any agonist that initiates a pro-inflammatory response by binding to mCD14 on the surface of cells or sCD14 in the circulation, such as for example, a damage-associated molecular pattern (DAMP) or pathogen-associated molecular pattern (PAMP) molecule and LPS. Non-limiting examples of DAMPs include, SOD1, TDP-43, members of the heat shock protein family as well as HMGB1, S100A, S100A9, S100B, α-synuclein, chromogranin, circulating DNA and RNA, amyloid and any other misfolded protein that arises as a result of mutation and which initiates a pro-inflammatory response by binding to mCD14 on the surface of cells or sCD14 in the circulation. Non-limiting examples of PAMPs include, LPS, other peptidoglycan and lipoteichoic acids of Gram-positive bacteria, lipoarabinomannan of mycobacteria and viral envelope proteins.

The term "antagonist antibody" is used in the broadest sense, and includes an antibody that inhibits or decreases the biological activity of an antigen to which the antibody binds (e.g., CD14). For example, an antagonist antibody may partially or completely block interaction between a receptor (e.g., CD14) and a ligand (e.g., a DAMP or PAMP), or may practically decrease the interaction due to tertiary structure change or down regulation of the receptor. Thus, a CD14 antagonist antibody encompasses antibodies that bind to CD14 and that block, inhibit, nullify, antagonize, suppress, decrease or reduce (including significantly), in any meaningful degree, a CD14 agonist activity, including activation of downstream pathways such as Toll-like receptor (TLR) signaling pathways (e.g., TLR4 signaling pathway) and the TIR-domain—containing adapter-inducing IFN-β (TRIF) pathway, or elicitation of a cellular response (e.g., production of pro-inflammatory mediators including pro-inflammatory cytokines) to CD14 binding by a CD14 ligand (e.g., a DAMP or PAMP).

The term "antibody" herein is used in the broadest sense and specifically covers naturally occurring antibodies, monoclonal antibodies, polyclonal antibodies, multispecific antibodies (e.g., bispecific antibodies), antibody fragments, or any other antigen-binding molecule so long as they exhibit the desired immuno-interactivity. A naturally occurring "antibody" includes within its scope an immunoglobulin comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised specific CH domains (e.g., CH1, CH2 and CH3). Each light chain is comprised of a light chain variable region (abbreviated herein as VL) and a light chain constant region. The light chain constant region is comprised of one domain, CL. The VH and VL regions can be further subdivided into regions of hypervariability, termed complementary determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, FR4. The constant regions of the antibodies may mediate the binding of an immunoglobulin to host tissues or factors, including various cells of the immune system (e.g., effector cells) and the first component (C1q) of the classical complement system. The antibodies can be of any isotype (e.g., IgG, IgE, IgM, IgD, IgA and IgY), class (e.g., IgG1, IgG2, IgG3, IgG4, IgA1 and IgA2), subclass or modified version thereof (e.g., IgG1 isotype, which carries L234A and L235A double mutations (IgG1-LALA)). The antibodies can be of any species, chimeric, humanized or human. In other embodiments, the antibody is a homomeric heavy chain antibody (e.g., camelid antibodies) which lacks the first constant region domain (CH1) but retains an otherwise intact heavy chain and is able to bind antigens through an antigen-binding domain. The variable regions of the heavy and light chains in the antibody-modular recognition domain (MRD) fusions will contain a functional binding domain that interacts with an antigen of interest.

The "variable domain" (variable domain of a light chain (VL), variable domain of a heavy chain (VH)) as used herein denotes each of the pair of light and heavy chain domains which are involved directly in binding the antibody to the antigen. The variable light and heavy chain domains have the same general structure and each domain comprises four FRs whose sequences are widely conserved, connected by three CDRs or "hypervariable regions". The FRs adopt a β-sheet conformation and the CDRs may form loops connecting the β-sheet structure. The CDRs in each chain are held in their three-dimensional structure by the FRs and form together with the CDRs from the other chain the antigen binding site.

The term "antigen-binding portion" when used herein refer to the amino acid residues of an antibody which are responsible for antigen-binding generally, which generally comprise amino acid residues from the CDRs. Thus, "CDR" or "complementarity determining region" (also referred to as "hypervariable region") are used interchangeably herein to refer to the amino acid sequences of the light and heavy chains of an antibody which form the three-dimensional loop structure that contributes to the formation of an antigen binding site. There are three CDRs in each of the variable regions of the heavy chain and the light chain, which are designated "CDR1", "CDR2", and "CDR3", for each of the variable regions. The term "CDR set" as used herein refers to a group of three CDRs that occur in a single variable region that binds the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as "Kabat CDRs". Chothia and coworkers (Chothia and Lesk, 1987. *J. Mol. Biol.* 196: 901-917; Chothia et al., 1989. *Nature* 342: 877-883) found that certain sub-portions within Kabat CDRs adopt nearly identical peptide backbone conformations, despite having great diversity at the level of amino acid sequence. These sub-portions were designated as "L1", "L2", and "L3", or "H1", "H2", and "H3", where the "L" and the "H" designate the light chain and the heavy chain regions, respectively. These regions may be referred to as "Chothia CDRs", which have boundaries that overlap with Kabat CDRs. Other boundaries defining CDRs overlapping with the Kabat CDRs have been described by Padlan (1995. *FASEB J.* 9: 133-139) and MacCallum (1996. *J. Mol. Biol.* 262(5): 732-745). Still other CDR boundary definitions may not strictly follow one of these systems, but will nonetheless overlap with the Kabat CDRs, although they may be shortened or lengthened in light of prediction or experimental findings that particular residues or groups of residues or even entire CDRs do not significantly impact antigen binding.

As used herein, the term "framework region" or "FR" refers to the remaining sequences of a variable region minus the CDRs. Therefore, the light and heavy chain variable domains of an antibody comprise from N- to C-terminus the domains FR1, CDR1, FR2, CDR2, FR3, CDR3, and FR4. CDRs and FRs are typically determined according to the standard definition of Kabat, E. A., et al., Sequences of Proteins of Immunological Interest, 5th ed., Public Health Service, National Institutes of Health, Bethesda, Md. (1991) and/or those residues from a "hypervariable loop".

As used herein, the terms "light chain variable region" ("VL") and "heavy chain variable region" (VH) refer to the regions or domains at the N-terminal portion of the light and heavy chains respectively which have a varied primary amino acid sequence for each antibody. The variable region of an antibody typically consists of the amino terminal domain of the light and heavy chains as they fold together to form a three-dimensional binding site for an antigen. Several subtypes of VH and VL, based on structural similarities, have been defined, for example as set forth in the Kabat database.

The term "chimeric antibody" refers to antibodies that comprise heavy and light chain variable region sequences from one species and constant region sequences from another species, such as antibodies having murine heavy and light chain variable regions linked to human constant regions.

"Humanized" forms of non-human (e.g., rodent) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Thus, the FRs and CDRs of a humanized antibody need not correspond precisely to the parental (i.e., donor) sequences, e.g., a donor antibody CDR or the consensus framework may be mutagenized by substitution, insertion, and/or deletion of at least one amino acid residue so that the CDR or FR at that site does not correspond to either the donor antibody or the consensus framework. Typically, such mutations, however, will not be extensive and will generally avoid "key residues" involved in binding to an antigen. Usually, at least 80%, preferably at least 85%, more preferably at least 90%, and most preferably at least 95% of the humanized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (see, for example, Winnaker, *From Genes to Clones* (Verlagsgesellschaft, Weinheim, 1987)). A "consensus immunoglobulin sequence" may thus comprise a "consensus framework region(s)" and/or a "consensus CDR(s)". In a family of immunoglobulins, each position in the consensus sequence is occupied by the amino acid occurring most frequently at that position in the family. If two amino acids occur equally frequently, either can be included in the consensus sequence. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al. (1986. *Nature* 321:522-525), Riechmann et al. (1988. *Nature* 332:323-329) and Presta (1992. *Curr. Op. Struct. Biol.* 2:593-596). A humanized antibody can be selected from any class of immunoglobulins, including IgM, IgG, IgD, IgA, and IgE, and any isotype, including without limitation IgG1, IgG2, IgG3, and IgG4. A humanized antibody may comprise sequences from more than one class or isotype, and particular constant domains may be selected to optimize desired effector functions using techniques well known in the art. As used herein, the term "key residue" refers to certain residues within the variable region that have more impact on the binding specificity and/or affinity of an antibody, in particular a humanized antibody. A key residue includes, but is not limited to, one or more of the following: a residue that is adjacent to a CDR, a potential glycosylation site (can be either N- or O-glycosylation site), a rare residue, a residue capable of interacting with the antigen, a residue capable of interacting with a CDR, a canonical residue, a contact residue between heavy chain variable region and light chain variable region, a residue within the Vernier zone, and a residue in the region that overlaps between the Chothia definition of a variable heavy chain CDR1 and the Kabat definition of the first heavy chain framework.

As used herein, "Vernier" zone refers to a subset of framework residues that may adjust CDR structure and fine-tune the fit to antigen as described by Foote and Winter (1992. *J. Mol. Biol.* 224: 487-499). Vernier zone residues form a layer underlying the CDRs and may impact on the structure of CDRs and the affinity of the antibody.

As used herein, the term "canonical" residue refers to a residue in a CDR or framework that defines a particular canonical CDR structure as defined by Chothia et al. (1987. *J. Mol. Biol.* 196: 901-917; 1992. *J. Mol. Biol.* 227: 799-817), both are incorporated herein by reference). According to Chothia et al., critical portions of the CDRs of many antibodies have nearly identical peptide backbone confirmations despite great diversity at the level of amino acid sequence. Each canonical structure specifies primarily a set of peptide backbone torsion angles for a contiguous segment of amino acid residues forming a loop.

As used herein, the terms "donor" and "donor antibody" refer to an antibody providing one or more CDRs to an "acceptor antibody". In some embodiments, the donor antibody is an antibody from a species different from the antibody from which the FRs are obtained or derived. In the context of a humanized antibody, the term "donor antibody" refers to a non-human antibody providing one or more CDRs.

As used herein, the terms "acceptor" and "acceptor antibody" refer to an antibody providing at least 80%, at least 85%, at least 90%, at least 95%, at least 98%, or 100% of the amino acid sequences of one or more of the FRs. In some embodiments, the term "acceptor" refers to the antibody amino acid sequence providing the constant region(s). In other embodiments, the term "acceptor" refers to the antibody amino acid sequence providing one or more of the FRs and the constant region(s). In specific embodiments, the term "acceptor" refers to a human antibody amino acid sequence that provides at least 80%, preferably, at least 85%, at least 90%, at least 95%, at least 98%, or 100% of the amino acid sequences of one or more of the FRs. In accordance with this embodiment, an acceptor may contain at least 1, at least 2, at least 3, least 4, at least 5, or at least 10 amino acid residues that does (do) not occur at one or more specific positions of a human antibody. An acceptor framework region and/or acceptor constant region(s) may be, for example, derived or obtained from a germline antibody gene, a mature antibody gene, a functional antibody (e.g., antibodies well-known in the art, antibodies in development, or antibodies commercially available).

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The terms "heavy chain variable region CDR1" and "H-CDR1" are used interchangeably, as are the terms "heavy chain variable region CDR2" and "H-CDR2", the terms "heavy chain variable region CDR3" and "H-CDR3", the terms "light chain variable region CDR1" and "L-CDR1"; the terms "light chain variable region CDR2" and "L-CDR2" and the terms "light chain variable region CDR3" and "L-CDR3" antibody fragment. Throughout the specification, complementarity determining regions ("CDR") are defined according to the Kabat definition unless specified otherwise. The Kabat definition is a standard for numbering the residues in an antibody and it is typically used to identify CDR regions (Kabat et al., (1991), 5th edition, NIH publication No. 91-3242).

Antigen binding can be performed by "fragments" or "antigen-binding fragments" of an intact antibody. Herein, both terms are used interchangeably. Examples of binding fragments encompassed within the term "antibody fragment" of an antibody include a Fab fragment, a monovalent fragment consisting of the VL, VH, CL and CH1 domains; a F(ab')2 fragment, a bivalent fragment comprising two Fab fragments linked by a disulfide bridge at the hinge region; an Fd fragment consisting of the VH and CH1 domains; an Fv fragment consisting of the VL and VH domains of a single arm of an antibody; a single domain antibody (dAb) fragment (Ward et al., 1989. Nature 341:544-546), which consists of a VH domain; and an isolated complementary determining region (CDR).

A "single chain variable Fragment (scFv)" is a single protein chain in which the VL and VH regions pair to form monovalent molecules (known as single chain Fv (scFv); see, e.g., Bird et al., 1988. Science 242:423-426; and Huston et al., 1988. Proc. Natl. Acad. Sci. 85:5879-5883). Although the two domains VL and VH are coded for by separate genes, they can be joined, using recombinant methods, by an artificial peptide linker that enables them to be made as a single protein chain. Such single chain antibodies include one or more antigen binding moieties. These antibody fragments are obtained using conventional techniques known to those of skill in the art, and the fragments are screened for utility in the same manner as are intact antibodies.

The term "monoclonal antibody" and abbreviations "MAb" and "mAb", as used herein, refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each mAb is directed against a single determinant on the antigen. The modifier "monoclonal" is not to be construed as requiring production of the antibody by any particular method. Monoclonal antibodies may be produced, for example, by a single clone of antibody-producing cells, including hybridomas. The term "hybridoma" generally refers to the product of a cell-fusion between a cultured neoplastic lymphocyte and a primed B- or T-lymphocyte which expresses the specific immune potential of the parent cell.

An antibody "that binds" an antigen of interest (e.g., CD14) is one that binds the antigen with sufficient affinity such that the antibody is useful as a therapeutic agent in targeting a cell or tissue expressing the antigen, and does not significantly cross-react with other proteins. In such embodiments, the extent of binding of the antibody to a "non-target" protein will be less than about 10% of the binding of the antibody, oligopeptide or other organic molecule to its particular target protein as determined, for example, by fluorescence activated cell sorting (FACS) analysis, enzyme-linked immunosorbent assay (ELISA), immunoprecipitation or radioimmunoprecipitation (RIA). Thus, an antibody that antagonizes CD14 to which it binds suitably inhibits or decreases production of pro-inflammatory mediators, including pro-inflammatory cytokines/chemokines. With regard to the binding of an antibody to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. The specific region of the antigen to which the antibody binds is typically referred to as an "epitope". The term "epitope" broadly includes the site on an antigen which is specifically recognized by an antibody or T-cell receptor or otherwise interacts with a molecule. Generally epitopes are of active surface groupings of molecules such as amino acids or carbohydrate or sugar side chains and generally may have specific three-dimensional structural characteristics, as well as specific charge characteristics. As will be appreciated by one of skill in the art, practically anything to which an antibody can specifically bind could be an epitope.

The term "cell" as used herein refers to any mammalian cell present outside the CNS that comprises mCD14 and produces pro-inflammatory mediators (e.g. cytokines). Non-limiting examples are immune cells, epithelial cells, osteoblasts, fibroblasts, and smooth muscle cells.

Throughout this specification, unless the context requires otherwise, the words "comprise", "comprises" and "comprising" will be understood to imply the inclusion of a stated step or element or group of steps or elements but not the exclusion of any other step or element or group of steps or elements. Thus, use of the term "comprising" and the like indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

Reference to "Dementia" as used herein refers to any disease which belongs to the syndrome in which there is deterioration in cognitive function (i.e. the ability to process thought) beyond what might be expected from normal ageing. Without limiting the present invention to any one disease, examples of Dementia include AD, the Lewy body dementias—dementia with Lewy bodies (DLB) and Parkinson's disease dementia, Vascular Dementia and Frontotemperol dementia (FTD).

By "effective amount", in the context of treating a condition is meant the administration of an amount of an agent or composition to an individual in need of such treatment or prophylaxis, either in a single dose or as part of a series, that is effective for the prevention of incurring a symptom, holding in check such symptoms, and/or treating existing symptoms, of that condition. The effective amount will vary depending upon the age, health and physical condition of the individual to be treated and whether symptoms of disease are apparent, the taxonomic group of individual to be treated, the formulation of the composition, the assessment of the medical situation, and other relevant factors. Optimal dosing schedules can be calculated from measurements of drug accumulation in the body of the subject. Optimum dosages may vary depending on the relative potency in an individual subject, and can generally be estimated based on EC50 values found to be effective in in vitro and in vivo animal models. Persons of ordinary skill can easily determine optimum dosages, dosing methodologies and repetition rates. It is expected that the amount will fall in a relatively broad range that can be determined through routine trials.

"Hybridization" is used herein to denote the pairing of complementary nucleotide sequences to produce a DNA-DNA hybrid or a DNA-RNA hybrid. Complementary base sequences are those sequences that are related by the base-pairing rules. In DNA, A pairs with T and C pairs with G. In RNA U pairs with A and C pairs with G. In this regard, the terms "match" and "mismatch" as used herein refer to the hybridization potential of paired nucleotides in complementary nucleic acid strands. Matched nucleotides hybridize efficiently, such as the classical A-T and G-C base pair mentioned above. Mismatches are other combinations of nucleotides that do not hybridize efficiently. In the present invention, the preferred mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances as known to those of skill in the art.

As used herein, the term "immune cell" refers to a cell belonging to the immune system which is present outside the CNS. Immune cells include cells of hematopoietic origin such as but not limited to T lymphocytes (T cells), B lymphocytes (B cells), natural killer (NK) cells, granulocytes, neutrophils, macrophages, monocytes, dendritic cells, and specialized forms of any of the foregoing, e.g., plasmacytoid dendritic cells, Langerhans cells, plasma cells, natural killer T (NKT) cells, T helper cells, and cytotoxic T lymphocytes (CTL).

Reference herein to "immuno-interactive" and its grammatical equivalents, includes reference to any interaction, reaction, or other form of association between molecules and in particular where one of the molecules is, or mimics, a component of the immune system.

The terms "inhibit", "inhibiting", "decrease" or "decreasing" and the like, in relation to "the production of pro-inflammatory mediators" by cells as used herein refers to at least a small but measurable reduction in the level or amount of pro-inflammatory mediator/s produced by a peripheral cell. In embodiments, the production of the pro-inflammatory mediator by a cell is inhibited or decreased by at least 20% over non-treated controls; in more embodiments, the inhibition or decrease is at least 50%; in still more embodiments, the inhibition or decrease is at least 70%, and in embodiments, the inhibition or decrease is at least 80%. Such reductions in pro-inflammatory mediator production are capable of reducing the deleterious effects of an inflammatory mediator cascade in in vivo embodiments.

A suitable in vitro assay (e.g. ELISA, RT-PCR) can be used to evaluate the efficacy of a CD14 antagonist antibody in inhibiting or decreasing the production of pro-inflammatory mediators by a peripheral cell. For example, competitive RT-PCR techniques can be used to measure the levels of cytokine mRNA obtained from within a cell, and the levels of expressed cytokine released from the cell can be measured by sandwich ELISA using, for example, one or more monoclonal antibodies which specifically bind to a particular cytokine. In vivo screening can also be performed by following procedures well known in the art. For example, a CD14 antagonist antibody is administered to an animal model (e.g., a mouse) and blood is collected to assess the levels of various cytokines. The skilled person would be well versed in the techniques available for the measurement of cytokine production. Based on the results, an appropriate dosage range and systemic administration route can also be determined.

By "isolated" is meant material that is substantially or essentially free from components that normally accompany it in its native state.

The term "ligand", as used herein, refers to any molecule which is capable of binding a receptor.

The phrase "motor neurone disease (MND)" as used herein, refers to a neurological disorder that selectively destroys motor neurones.

The phrase "neurodegenerative disease" means a disease characterized by progressive nervous system dysfunction. Neurodegenerative diseases include a heterogeneous group of diseases of the central or peripheral nervous system that have many different etiologies. Such conditions can be, without limitation, hereditary, secondary to toxic or metabolic processes, and can result from infection. Neurodegenerative conditions are progressive conditions that can be age associated or chronic. Such conditions can be characterized by abnormalities of relatively specific regions of the brain or specific populations of neurons. The particular cell groups affected in different neurodegenerative conditions typically determine the clinical phenotype of the condition. In particular, neurodegenerative conditions can be associated with atrophy of a particular affected central or peripheral nervous system structure.

Exemplary neurodegenerative diseases or conditions include, but are not limited to, Motor Neurone Diseases (MNDs), including amyotrophic lateral sclerosis (ALS) also known as Lou Gehrig's Disease, primary lateral sclerosis (PLS), progressive muscular atrophy (PMA), progressive bulbar palsy (PBP) and pseudobulbar palsy. Other exemplary neurodegenerative diseases or conditions include Dementia such as Alzheimer's disease, Parkinsonian Syndromes, Lewy-body dementia (DLB and PDD), Vascular dementia, Frontotemporal dementia, mesolimbocortical dementia, familial dementia with spastic paraparesis and AIDS related dementia.

Other exemplary neurodegenerative diseases include Parkinson's disease, spinal muscular atrophies, inherited forms of spinal muscular atrophy, Charcot-Marie-Tooth Disorders, Kennedy disorder and post-polio syndrome multiple sclerosis, diffuse cerebral cortical atrophy, Pick disease, thalamic degeneration, Huntington chorea, cortical-striatal-spinal degeneration, cortical-basal ganglionic degeneration, cerebrocerebellar degeneration, polyglucosan body disease, Shy-Drager syndrome, olivopontocerebellar atrophy, progressive supranuclear palsy, dystonia musculorum deformans, Hallervorden-Spatz disease, Meige syndrome, familial tremors, Gilles de la Tourette syndrome, acanthocytic chorea, Friedreich ataxia, Holmes familial cortical cerebellar atrophy, Gerstmann-Straussler-Scheinker disease, hereditary muscular atrophy, spastic paraplegia, peroneal muscular atrophy, hypertrophic interstitial polyneuropathy, heredopathia atactica polyneuritiformis, optic neuropathy. The skilled person understands that these and other mild, moderate or severe neurodegenerative conditions in which an underlying inflammatory component contributes to disease pathology can be treated according to the method of the invention.

It is common for people to have mixed dementia—a combination of two or more diseases, at least one of which is Dementia. For example, some people have both Alzheimer's disease and Vascular Dementia, a small number of people affected by FTD also develop Motor Neurone Disease (FTD/MND), (sometimes called FTD with Amyotrophic Lateral Sclerosis or FTD/ALS). It should, therefore, also be understood that reference to a "neurodegenerative disease" as used herein is reference to the subject diagnosed with or at risk of developing one or more neurodegenerative diseases.

The terms "patient", "subject", or "individual" used interchangeably herein, refer to any subject, particularly a vertebrate subject, and even more particularly a mammalian subject that has been diagnosed with a neurodegenerative disease or identified as having an increased likelihood of developing a neurodegenerative disease. The patient may be healthy or showing preliminary signs of a neurodegenerative disease, such as, but not linked to muscle fatigue or memory loss. Alternatively, the subject may have a genetic predisposition to the disease.

Whilst the "subject" is generally a human subject, the treatment of development or progression of neurodegenerative diseases and conditions can also be important such as in the treatment of horses for equine motor neurone disease, dogs for canine spinal muscular atrophy and in undertaking animal studies. Hence, reference herein to a "patient", "subject" or "individual" includes a human and non-human mammal such as but not limited to horses, companion animals such as dogs and cats, and laboratory test animals such as mice, rats, guinea pigs, hamsters, rabbits, pigs and non-human primates.

As used herein, the term "systemic administration" or "administered systemically" or "systemically administered" means introducing an agent into a subject outside of the central nervous system. Systemic administration encompasses any route of administration other than direct administration to the spine or brain. As such, it is clear that intrathecal and epidural administration as well as cranial injection or implantation, are not within the scope of the terms "systemic administration", "administered systemically" or "systemically administered". It will be understood that systemic administration does not preclude a therapeutic effect from occurring in the CNS.

A pharmaceutical composition useful in the invention can be systemically administered, for example, orally in any acceptable form such as in a tablet, liquid, capsule, powder, or the like; by intravenous, intraperitoneal, intramuscular, subcutaneous or parenteral injection; by transdermal diffusion or electrophoresis; and by minipump or other implanted extended release device or formulation. According to some embodiments, the systemic administration is carried out by a route selected from the group consisting of: intraperitoneal, intravenous, subcutaneous and intranasal administration, and combinations thereof.

Reference to "periphery" as used herein includes any part of the body (which is not part of the CNS) in which cells expressing mCD14, or where circulating sCD14, are found, including, for example, the circulatory system (e.g. the cardiovascular system and the lymphatic system) and the peripheral nervous system.

By "pharmaceutically acceptable carrier" is meant a pharmaceutical vehicle comprised of a material that is not biologically or otherwise undesirable, i.e., the material may be administered to a subject along with the selected active agent without causing any or a substantial adverse reaction. Carriers may include excipients and other additives such as diluents, detergents, coloring agents, wetting or emulsifying agents, pH buffering agents, preservatives, transfection agents and the like.

Similarly, a "pharmacologically acceptable" salt, ester, amide, prodrug or derivative of a compound as provided herein is a salt, ester, amide, prodrug or derivative that this not biologically or otherwise undesirable.

The terms "polynucleotide," "genetic material," "genetic forms," "nucleic acids" and "nucleotide sequence" include RNA, cDNA, genomic DNA, synthetic forms and mixed polymers, both sense and antisense strands, and may be chemically or biochemically modified or may contain non-natural or derivatized nucleotide bases, as will be readily appreciated by those skilled in the art.

The term "pro-inflammatory mediator" means an immunoregulatory agent that favors inflammation. Such agents include, cytokines such as chemokines, interleukins (IL), lymphokines, and tumor necrosis factor (TNF) as well as growth factors. In specific embodiments, the pro-inflammatory mediator is a "pro-inflammatory cytokine". Typically, pro-inflammatory cytokines include IL-la, IL-1B, IL-6, and TNF-α, which are largely responsible for early responses. Other pro-inflammatory mediators include LIF, IFN-γ, IFN-β, IFN-α, OSM, CNTF, TGF-β, GM-CSF, TWEAK, IL-11, IL-12, IL-15, IL-17, IL-18, IL-19, IL-20, IL-8, IL-16, IL-22, IL-23, IL-31 and IL-32 (Tato et al., 2008. *Cell* 132:900; *Cell* 132:500, *Cell* 132:324). Pro-inflammatory mediators may act as endogenous pyrogens (IL-1, IL-6, IL-17, TNF-α), up-regulate the synthesis of secondary mediators and pro-inflammatory cytokines by both macrophages and mesenchymal cells (including fibroblasts, epithelial and endothelial cells), stimulate the production of acute phase proteins, or attract inflammatory cells. In specific embodiments, the term "pro-inflammatory cytokine" relates to TNF-α, IL-1 α, IL-6, IFNβ, IL-1B, IL-8, IL-17 and IL-18.

The term "receptor" denotes a cell-associated protein that binds to a bioactive molecule termed a "ligand". This interaction mediates the effect of the ligand on the cell. In general, the binding of ligand to receptor results in a conformational change in the receptor that causes an interaction between the receptor and other molecule(s) on the surface of the cell or in the interior of the cell, which in turn leads to an alteration in the metabolism of the cell. Metabolic events that are often linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids, hydrolysis of phospholipids and modulation of a cellular pathway (e.g., stimulation or inhibition of production of one or more pro-inflammatory mediators).

The term "sequence identity" as used herein refers to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. For the purposes of the present invention, "sequence identity" will be understood to mean the "match percentage" calculated by an appropriate method. For example, sequence identity analysis may be carried out using the DNASIS computer program (Version 2.5 for windows; available from Hitachi Software engineering Co., Ltd., South San Francisco, California, USA) using standard defaults as used in the reference manual accompanying the software.

"Similarity" refers to the percentage number of amino acids that are identical or constitute conservative substitutions as defined in Table 1.

TABLE 1

| ORIGINAL RESIDUE | EXEMPLARY SUBSTITUTIONS |
|---|---|
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile, |
| Phe | Met, Leu, Tyr |
| Ser | Thr |
| Thr | Ser |
| Trp | Tyr |
| Tyr | Trp, Phe |
| Val | Ile, Leu |

Similarity may be determined using sequence comparison programs such as GAP (Deveraux et al., 1984. *Nucleic Acids Res.* 12, 387-395). In this way, sequences of a similar or substantially different length to those cited herein might be compared by insertion of gaps into the alignment, such gaps being determined, for example, by the comparison algorithm used by GAP.

Terms used to describe sequence relationships between two or more polynucleotides or polypeptides include "reference sequence", "comparison window", "sequence identity", "percentage of sequence identity" and "substantial identity". A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, WI, USA) or by inspection and the best alignment (i.e., resulting in the highest percentage homology over the comparison window) generated by any of the various methods selected. Reference also may be made to the BLAST family of programs as for example disclosed by Altschul et al., 1997. *Nucleic Acids Res.* 25:3389. A detailed discussion of sequence analysis can be found in Unit 19.3 of Ausubel et al., "Current Protocols in Molecular Biology," John Wiley & Sons Inc, 1994-1998, Chapter 15.

"Stringency" as used herein refers to the temperature and ionic strength conditions, and presence or absence of certain organic solvents, during hybridization. The higher the stringency, the higher will be the observed degree of complementarity between sequences. "Stringent conditions" as used herein refers to temperature and ionic conditions under which only polynucleotides having a high proportion of complementary bases, preferably having exact complementarity, will hybridize. The stringency required is nucleotide sequence dependent and depends upon the various components present during hybridization, and is greatly changed when nucleotide analogues are used. Generally, stringent conditions are selected to be about 10° C. to 20° C. less than the thermal melting point (Tm) for the specific sequence at a defined ionic strength and pH. The Tm is the temperature (under defined ionic strength and pH) at which 50% of a target sequence hybridizes to a complementary probe. It will be understood that a polynucleotide will hybridize to a target sequence under at least low stringency conditions, preferably under at least medium stringency conditions and more preferably under high stringency conditions. Reference herein to low stringency conditions include and encompass from at least about 1% v/v to at least about 15% v/v formamide and from at least about 1 M to at least about 2 M salt for hybridization at 42° C., and at least about 1 M to at least about 2 M salt for washing at 42° C. Low stringency conditions also may include 1% Bovine Serum Albumin (BSA), 1 mM EDTA, 0.5 M NaHPO4 (pH 7.2), SDS for hybridization at 65° C., and (i) 2×SSC, 0.1% SDS; or (ii) 7% 0.5% BSA, 1 mM EDTA, 40 mM NaHPO4 (pH 7.2), 5% SDS for washing at room temperature. Medium stringency conditions include and encompass from at least about 16% v/v to at least about 30% v/v formamide and from at least about 0.5 M to at least about 0.9 M salt for hybridization at 42° C., and at least about 0.5 M to at least about 0.9 M salt for washing at 42° C. Medium stringency conditions also may include 1% Bovine Serum Albumin (BSA), 1 mM EDTA, 0.5 M NaHPO4 (pH 7.2), 7% SDS for hybridization at 65° C., and (i) 2×SSC, 0.1% SDS; or (ii) 0.5% BSA, 1 mM EDTA, 40 mM NaHPO4 (pH 7.2), 5% SDS for washing at 42° C. High stringency conditions include and encompass from at least about 31% v/v to at least about 50% v/v formamide and from at least about 0.01 M to at least about 0.15 M salt for hybridization at 42° C., and at least about 0.01 M to at least about 0.15 M salt for washing at 42° C. High stringency conditions also may include 1% BSA, 1 mM EDTA, 0.5 M NaHPO4 (pH 7.2), 7% SDS for hybridization at 65° C., and (i) 0.2×SSC, 0.1% SDS; or (ii) 0.5% BSA, 1 mM EDTA, 40 mM NaHPO4 (pH 7.2), 1% SDS for washing at a temperature in excess of 65° C. One embodiment of high stringency conditions includes hybridizing in 6×SSC at about 45° C., followed by one or more washes in 0.2×SSC, 0.1% SDS at 65° C. One embodiment of very high stringency conditions includes hybridizing 0.5 M sodium phosphate, 7% SDS at 65° C., followed by one or more washes at 0.2×SSC, 1% SDS at 65° C. Other stringent conditions are well known in the art. A skilled addressee will recognize that various factors can be manipulated to optimize the specificity of the hybridization. Optimization of the stringency of the final washes can serve to ensure a high degree of hybridization. For detailed examples, see CURRENT PROTOCOLS IN MOLECULAR BIOLOGY (supra) at pages 2.10.1 to 2.10.16 and MOLECULAR CLONING. A LABORATORY MANUAL (Sambrook et al., eds.) (Cold Spring Harbor Press 1989) at sections 1.101 to 1.104.

As used herein, reference to a "symptom" of a neurodegenerative disease is the a physical or mental feature which is regarded as indicating a disease. Non-limiting MND-mediated disease symptoms include progressive muscle atrophy, paralysis, spasticity, hyperreflexia, and other symptoms such as difficulty swallowing, limb weakness, slurred speech, impaired gait, facial weakness, respiratory changes and muscle cramps. Non-limiting dementia disease symptoms include difficulty remembering recent conversations, names or events; apathy and depression (early symptoms), impaired communication, poor judgment, disorientation, confusion, behavior changes and difficulty speaking, swallowing and walking (later symptoms). Examples of other symptoms which may indicate or be associated with a neurodegenerative disease include, for example, hallucinations, sleep disorders, movement symptoms and neuroleptic sensitivity. Typically, a subject will present with one or several symptoms depending on the disease and the individual subject. Determination of which symptoms are regarded as indicating a particular neurodegenerative disease would be well within the skill of those in the art.

As used herein, the terms "treatment", "treating", and the like, refer to obtaining a desired pharmacologic and/or physiologic effect in a subject in need of treatment, that is, a subject who has a neurodegenerative disease or is diagnosed as having a neurodegenerative disease or a subject at risk of developing a neurodegenerative disease. By "treatment" is meant:

(a) delaying development and/or progression of a neurodegenerative disease;

(b) ameliorating symptoms of a neurodegenerative disease;

(c) suppressing a neurodegenerative disease or its symptoms; and/or (d) improving or prolonging quality of life.

Reference to "treatment", "treat" or "treating" does not necessarily mean to cure the subject or prevent disease progression indefinitely. The subject may ultimately succumb to the neurodegenerative disease, however, the quality of life is extended for a period longer than without treatment since the development of the disease or condition is delayed.

Indicia of successful "treatment", includes any objective or subjective parameter such as abatement; remission; diminishing of memory or condition more tolerable to the patient; slowing in the rate of degeneration or decline or worsening of the illness; making the final point of worsening less debilitating; or improving a subject's physical or mental well-being. The treatment or amelioration of symptoms can be based on objective or subjective parameters; including the results of a physical examination, neurological examination, and/or psychiatric evaluations.

As used herein, underscoring or italicizing the name of a gene shall indicate the gene, in contrast to its protein product, which is indicated by the name of the gene in the absence of any underscoring or italicizing. For example, "CD14" shall mean the CD14 gene, whereas "CD14" shall indicate the protein product or products generated from transcription and translation and/or alternative splicing of the "CD14" gene.

Each embodiment described herein is to be applied mutatis mutandis to each and every embodiment unless specifically stated otherwise.

2. Compositions and Methods for Treating the Development or Progression of a Neurodegenerative Disease or Symptom Thereof The present invention provides methods and compositions that include a CD14 antagonist antibody for treating the development or progression of a neurodegenerative disease, or a symptom thereof.

2.1 CD14 Antagonist Antibodies

The present invention contemplates any CD14 antagonist antibody that binds to CD14 (e.g. mCD14 or sCD14) and blocks the binding of a DAMP or PAMP to CD14 and/or that binds to CD14 and inhibits or decreases a CD14 agonist-mediated response resulting in the production of pro-inflammatory mediators, including the production of pro-inflammatory cytokines. In some embodiments, a CD14 antagonist antibody of the present invention inhibits binding of a CD14 agonist, suitably a DAMP or PAMP, to CD14 thus inhibiting or decreasing the production of pro-inflammatory cytokines. In illustrative examples of this type, the CD14 antagonist antibody is selected from the 3C10 antibody that binds an epitope comprised in at least a portion of the region from amino acid 7 to amino acid 14 of human CD14 (van Voohris et al., 1983. *J. Exp. Med.* 158: 126-145; Juan et al., 1995. *J. Biol. Chem.* 270(29): 17237-17242), the MEM-18 antibody that binds an epitope comprised in at least a portion of the region from amino acid 57 to amino acid 64 of CD14 (Bazil et al., 1986. *Eur. J. Immunol.* 16(12):1583-1589; Juan et al., 1995. *J. Biol. Chem.* 270(10): 5219-5224), the 4C1 antibody (Adachi et al., 1999. *J. Endotoxin Res.* 5: 139-146; Tasaka et al., 2003. *Am. J. Respir. Cell. Mol. Biol.;* 2003. 29(2): 252-258), as well as the 28C5 and 23G4 antibodies that inhibit binding of LPS and suppress production of pro-inflammatory cytokines, and the 18E12 antibody that partly inhibits binding of LPS and suppresses production of pro-inflammatory cytokines (U.S. Pat. Nos. 5,820,858, 6,444, 206 and 7,326,569 to Leturcq et al.). In some embodiments, a CD14 antagonist antibody of the present invention inhibits binding of CD14 to a TLR such as TLR4, thereby blocking CD14-agonist mediated response, illustrative examples of which include the F1024 antibody disclosed in International Publication WO2002/42333. Each of the above references relating to CD14 antagonist antibodies is incorporated herein by reference in its entirety. The CD14 antagonist antibody may be a full-length immunoglobulin antibody or an antigen-binding fragment of an intact antibody, representative examples of which include a Fab fragment, a F(ab')2 fragment, an Fd fragment consisting of the VH and CH1 domains, an Fv fragment consisting of the VL and VH domains of a single arm of an antibody, a single domain antibody (dAb) fragment (Ward et al., 1989. *Nature* 341: 544-546), which consists of a VH domain; and an isolated CDR. Suitably, CD14 antagonist antibody is a chimeric, humanized or human antibody.

In some embodiments, the CD14 antagonist antibody is selected from the antibodies disclosed in U.S. Pat. No. 5,820,858:

(1) an antibody comprising:

a VL domain comprising, consisting or consisting essentially of the sequence:

```
(3C10 VL)
                                          [SEQ ID NO: 1]
QSPASLAVSLGQRATISC RASESVDSFGNSFMH WYQQKAGQPPKSSIY

RAANLES GIPARFSGSGSRTDFTLTINPVEADDVATYFC QQSYEDPWT

FGGGTKLGNQ;
``` and a VH domain comprising, consisting or consisting essentially of the sequence:

```
        (3C10 VH)
                                          [SEQ ID NO: 2]
    LVKPGGSLKLSCVASGFTFS SYAMS WVRQTPEKRLEWVA

SISSGGTTYYPDNVKG

RFTISRDNARNILYLQMSSLRSEDTAMYYCAR GYYDYHY

WGQGTTLTVSS;
```

(2) an antibody comprising:

a VL domain comprising, consisting or consisting essentially of the sequence:

```
(28C5 VL)
                                          [SEQ ID NO: 3]
QSPASLAVSLGQRATISC RASESVDSYVNSFLH WYQQKPGQPPKLLIY

RASNLQS GIPARFSGSGSRTDFTLTINPVEADDVATYCC QQSNEDPTT

FGGGTKLEIK;
``` and a VH domain comprising, consisting or consisting essentially of the sequence:

```
(28C5 VH)
                                          [SEQ ID NO: 4]
LQQSGPGLVKPSQSLSLTCTVTGYSIT SDSAWN WIRQFPGNRLEWMG

YISYSGSTSYNPSLKS RISITRDTSKNQFFLQLNSVTTEDTATYYCVR

GLRFAY WGQGTLVTVSA;
``` and (3) an antibody comprising:

a VL domain comprising, consisting or consisting essentially of the sequence:

```
(18E12 VL)
                                          [SEQ ID NO: 5]
QTPSSLSASLGDRVTISC RASQDIKNYLN WYQQPGGTVKVLIY

YTSRLHS GVPSRFSGSGSGTDYSLTISNLEQEDFATYFC

QRGDTLPWT FGGGTKLEIK;
``` and
a VH domain comprising, consisting or consisting essentially of the sequence:

```
(18E12 VH)
                                          [SEQ ID NO: 6]
LESGPGLVAPSQSLSITCTVSGFSLT NYDIS WIRQPPGKGLEWLG

VIWTSGGTNYNSAFMS RLSITKDNSESQVFLKMNGLQTDDTGIYYCVR

GDGNFYLYNFDY WGQGTTLTVSS;
```

Also contemplated are antibodies that comprise the VL and VH CDR sequences of the above antibodies, representative embodiments of which include:
  (1) an antibody that comprises: a) an antibody VL domain, or antigen binding fragment thereof, comprising L-CDR1, L-CDR2 and L-CDR3, wherein: L-CDR1 comprises the sequence RASESVDSFGNSFMH [SEQ ID NO: 7] (3C10 L-CDR1); L-CDR2 comprises the sequence RAANLES [SEQ ID NO: 8] (3C10 L-CDR2); and L-CDR3 comprises the sequence QQSYEDPWT [SEQ ID NO: 9] (3C10 L-CDR3); and b) an antibody VH domain, or antigen binding fragment thereof, comprising H-CDR1, H-CDR2 and H-CDR3, wherein: H-CDR1 comprises the sequence SYAMS [SEQ ID NO: 10] (3C10 H-CDR1); H-CDR2 comprises the sequence SISSGGTTYYPDNVKG [SEQ ID NO: 11] (3C10 H-CDR2); and H-CDR3 comprises the sequence GYYDYHY [SEQ ID NO: 12] (3C10 H-CDR3);
  (2) an antibody that comprises: a) an antibody VL domain, or antigen binding fragment thereof, comprising L-CDR1, L-CDR2 and L-CDR3, wherein: L-CDR1 comprises the sequence RASESVDSYVNSFLH [SEQ ID NO: 13] (28C5 L-CDR1); L-CDR2 comprises the sequence RASNLQS [SEQ ID NO: 14] (28C5 L-CDR2); and L-CDR3 comprises the sequence QQSNEDPTT [SEQ ID NO: 15] (28C5 L-CDR3); and b) an antibody VH domain, or antigen binding fragment thereof, comprising H-CDR1, H-CDR2 and H-CDR3, wherein: H-CDR1 comprises the sequence SDSAWN [SEQ ID NO: 16] (28C5 H-CDR1); H-CDR2 comprises the sequence YISYSGSTSYNPSLKS [SEQ ID NO: 17] (28C5 H-CDR2); and H-CDR3 comprises the sequence GLRFAY [SEQ ID NO: 18] (28C5 H-CDR3); and
  (3) an antibody that comprises: a) an antibody VL domain, or antigen binding fragment thereof, comprising L-CDR1, L-CDR2 and L-CDR3, wherein: L-CDR1 comprises the sequence RASQDIKNYLN [SEQ ID NO: 19] (18E12 L-CDR1); L-CDR2 comprises the sequence YTSRLHS [SEQ ID NO: 20] (18E12 L-CDR2); and L-CDR3 comprises the sequence QRGDTLPWT [SEQ ID NO: 21] (18E12 L-CDR3); and b) an antibody VH domain, or antigen binding fragment thereof, comprising H-CDR1, H-CDR2 and H-CDR3, wherein: H-CDR1 comprises the sequence NYDIS [SEQ ID NO: 22] (18E12 H-CDR1); H-CDR2 comprises the sequence VIWTSGGTNYNSAFMS [SEQ ID NO: 23] (18E12 H-CDR2); and H-CDR3 comprises the sequence GDGNFYLYNFDY [SEQ ID NO: 24] (18E12 H-CDR3).

In some embodiments, the CD14 antagonist antibody is humanized. In illustrative examples of this type, the humanized CD14 antagonist antibodies suitably comprise a donor CDR set corresponding to a CD14 antagonist antibody (e.g., one of the CD14 antagonist antibodies described above), and a human acceptor framework. The human acceptor framework may comprise at least one amino acid substitution relative to a human germline acceptor framework at a key residue selected from the group consisting of: a residue adjacent to a CDR; a glycosylation site residue; a rare residue; a canonical residue; a contact residue between heavy chain variable region and light chain variable region; a residue within a Vernier zone; and a residue in a region that overlaps between a Chothia-defined VH CDR1 and a Kabat-defined first heavy chain framework. Techniques for producing humanized mAbs are well known in the art (see, for example, Jones et al., 1986. *Nature* 321: 522-525; Riechmann et al. 1988. *Nature* 332:323-329; Verhoeyen et al., 1988. *Science* 239: 1534-1536; Carter et al., 1992. *Proc. Natl. Acad. Sci. USA* 89: 4285-4289; Sandhu, J S., 1992. *Crit. Rev. Biotech.* 12: 437-462, and Singer et al., 1993. *J. Immunol.* 150: 2844-2857). A chimeric or murine monoclonal antibody may be humanized by transferring the mouse CDRs from the heavy and light variable chains of the mouse immunoglobulin into the corresponding variable domains of a human antibody. The mouse framework regions (FR) in the chimeric monoclonal antibody are also replaced with human FR sequences. As simply transferring mouse CDRs into human FRs often results in a reduction or even loss of antibody affinity, additional modification might be required in order to restore the original affinity of the murine antibody. This can be accomplished by the replacement of one or more human residues in the FR regions with their murine counterparts to obtain an antibody that possesses good binding affinity to its epitope. See, for example, Tempest et al. (1991. *Biotechnology* 9:266-271) and Verhoeyen et al. (1988 supra). Generally, those human FR amino acid residues that differ from their murine counterparts and are located close to or touching one or more CDR amino acid residues would be candidates for substitution.

In a preferred embodiment, the CD14 antagonist antibody is the IC14 antibody (Axtelle et al., 2001. *J. Endotoxin Res.* 7: 310-314; and U.S. Pat. Pub. No. 2006/0121574, which are incorporated herein by reference in their entirety) or an antigen-binding fragment thereof. The IC14 antibody is a chimeric (murine/human) monoclonal antibody that specifically binds to human CD14. The murine parent of this antibody is 28C5 noted above (see, U.S. Pat. Nos. 5,820,858, 6,444,206 and 7,326,569 to Leturcq et al., and Leturcq et al., 1996. *J. Clin. Invest.* 98: 1533-1538). The IC14 antibody comprises a VL domain and a VH domain, wherein:

the VL domain comprises the amino acid sequence:

```
                                         [SEQ ID NO: 25]
METDTILLWVLLLWVPGSTGDIVLTQSPASLAVSLGQRATISCRASESV

DSYVNSFLHWYQQKPGQPPKLLIYRASNLQSGIPARFSGSGSRTDFTLT

INPVEADDVATYYCQQSNEDPYTFGGGTKLEIKRTVAAPSVFIFPPSDE

QLKSGTASVVCLLNNFYPREAKVQWKVDNALQSGNSQESVTEQDSKDST

YSLSSTLTLSKADYEKHKVYACEVTHQGLSSPVTKSFNRGEC;
``` and
the VH domain comprises the amino acid sequence:

[SEQ ID NO: 26]
MKVLSLLYLLTAIPGILSDVQLQQSGPGLVKPSQSLSLTCTVTGYSITS

DSAWNWIRQFPGNRLEWMGYISYSGSTSYNPSLKSRISITRDTSKNQFF

LQLNSVTTEDTATYYCVRGLRFAYWGQGTLVTVSSASTKGPSVFPLAPC

SRSTSESTAALGCLVKDYFPEPVTVSWNSGALTSGVHTFPAVLQSSGLY

SLSSVVTVPSSSLGTKTYTCNVDHKPSNTKVDKRVESKYGPPCPSCPAP

EFLGGPSVFLFPPKPKDTLMISRTPEVTCVVVDVSQEDPEVQFNWYVDG

VEVHNAKTKPREEQFNSTYRVVSVLTVLHQDWLNGKEYKCKVSNKGLPS

SIEKTISKAKGQPREPQVYTLPPSQEEMTKNQVSLTCLVKGFYPSDIAV

EWESNGQPENNYKTTPPVLDSDGSFFLYSRLTVDKSRWQEGNVFSCSVM

HEALHNHYTQKSLSLSLGK.

2.2 Screening Methods

The present invention also provides methods for the identification of antagonist antibodies of CD14 suitable for use in the treatment of the development or progression of a neurodegenerative disease or symptom thereof. These methods generally comprise determining whether a test agent is capable of directly antagonizing CD14. For example, the methods may involve determining whether a test agent is capable of inhibiting or decreasing the amount or agonist activity of CD14, wherein the ability to inhibit or decrease the amount or agonist activity of CD14 indicates that the test agent may be suitable for use in treating the development or progression of a neurodegenerative disease or symptom thereof as described herein. In some embodiments, the test agent is contacted with CD14, or a cell that expresses CD14 on its surface, or a nucleic acid sequence from which CD14 is expressed, suitably in the presence of a CD14 agonist such as a DAMP or PAMP, wherein a decrease in the amount or agonist activity of CD14 in the presence of the agonist, when compared to a control, indicates that the test agent binds to CD14 and directly antagonizes CD14. A decrease or inhibition of CD14 agonist activity, includes for example inhibiting, or decreasing activation of downstream pathways such as TLR signaling pathways (e.g., TLR4 signaling pathway) and the TRIF pathway, or elicitation of a cellular response (e.g., production of pro-inflammatory mediators including pro-inflammatory cytokines). In an embodiment, binding of the antagonist antibody to a peripheral cell expressing mCD14 or to sCD14 in a subject inhibits or decreases the production of one or more pro-inflammatory cytokines associated with disease pathology.

The screening methods of the invention may be carried out in vivo, ex vivo or in vitro. In particular, the step of contacting a test agent with CD14 or with a cell that expresses CD14 on its surface (e.g., immune cells) may be carried out in vivo, ex vivo or in vitro. The screening methods of the invention may be carried out in a cell-based or a cell-free system. For example, the screening method of the invention may comprise a step of contacting a cell expressing CD14 on its surface with a test agent and determining whether the contacting of the cell with the test agent leads to a decrease in the amount or agonist activity of CD14.

In such a cell-based assay, the CD14 and/or the test agent may be endogenous to the host cell, may be introduced into a host cell or tissue, may be introduced into the host cell or tissue by causing or allowing the expression of an expression construct or vector or may be introduced into the host cell by stimulating or activating expression from an endogenous gene in the cell. In such a cell-based method, the amount of activity of CD14 may be assessed in the presence or absence of a test agent in order to determine whether the agent is altering the amount of CD14 in the cell, such as through regulation of CD14 expression in the cell or through destabilization of CD14 protein within the cell, or altering the CD14 agonist activity of the cell. The presence of a lower CD14 agonist activity or a decreased amount of CD14 on the cell surface in the presence of the test agent indicates that the test agent may be a suitable antagonist of CD14 for use in accordance with the present invention in the treatment of an individual with a neurodegenerative disease or symptom thereof.

In one embodiment, such a cell-based assay may be carried out in vitro or ex vivo on cells or tissue deriving from the patient to be treated. It may therefore be determined whether or not the test agent is capable of decreasing the activity or amount of CD14 in the cells of that subject. In an embodiment the cells are stem cells or macrophage.

In preferred embodiments, the methods further comprise determining whether the test agent lacks substantial or detectable bind to another cellular component, suitably a binding partner of CD14, such as a CD14 binding partner that is either secreted (e.g., MD2) or located on the cell membrane (e.g., TLR4), to thereby determine that the test agent is a specific antagonist of CD14. In a non-limiting example of this type, the test agent is contacted in the presence of a CD14 agonist such as a DAMP or PAMP (1) with a wild-type cell that expresses CD14 on its surface (e.g., an immune cell such a macrophage), and (2) with a CD14 negative cell (e.g., an immune cell that is the same as in (1) but has a loss of function in the CD14 gene). If the test agent inhibits a CD14 agonist activity of the wild-type cell but not of the CD14 negative cell, this indicates that the test agent is a CD14 specific antagonist. Cells of this type may be constructed using routine procedures or animals.

In other embodiments, the screening methods of the invention may use a cell-free assay. For example, the CD14 may be present in a cell-free environment. A suitable cell-free assay may be carried out in a cell extract. For example, the contacting steps of the methods of the invention may be carried out in extracts obtained from cells that may express, produce or otherwise contain CD14 and/or a test agent. A cell-free system comprising CD14 may be incubated with the other components of the methods of the invention such a test agent.

The contacting step(s) of the method of the invention may comprise incubation of the various components. Such incubations may be performed at any suitable temperature, typically between 4° C. and 40° C. Incubation periods may be selected for optimum activity, but may also be optimized to facilitate rapid high-throughput screening. Following the contact and optional incubation steps, the subject methods may further include a washing step to remove unbound components, where such a washing step is generally employed when required to remove label that would give rise to a background signal during detection, such as radioactive or fluorescently labeled non-specifically bound components.

Incubation in cell-based or cell-free assay systems may be performed in a microtiter plate (e.g., a 96-well plate or other microwell plate). Further, incubation may be performed in an automated fashion (e.g., for high-throughput screening).

A screening method of the invention may be carried out in vivo. For example, a screening method may be carried out in an animal model. In such an in vivo model, the effects of a test agent may be assessed in the circulation (e.g., blood), or in other organs such as the liver, kidney or heart. Suitably, the animal is a non-human animal such as a mouse or rat. Such a model may be used to assess the in vivo effects of a test agent. For example, such a model may be used to assess whether the test agent is capable of decreasing the activity or amount of CD14 in vivo. In such a method, the amount and/or agonist activity of CD14 may be assessed.

An in vivo model may also be used to determine whether the test agent has any unwanted side effects. For example, a method of the invention may compare the effects of a test agent on CD14 with its effects on other receptors or cellular components (e.g., CD14 binding partners such as MD2 and TLR4) in order to determine whether the test agent is specific. In vivo animal models of MND are well known to the person skilled in the art.

In an in vivo model as described herein, or an in vitro model such as a cell-based or cell-free assay model as described herein, the effects of a test agent on CD14 may be compared with the effects of the same agent on cellular components including CD14 binding partners such as MD2 and TLR4. As discussed above, a desirable CD14 antagonist antibody for use in a method of treatment and prophylaxis as described herein may be an antibody that specifically antagonizes CD14. The screening methods of the invention may thus include an additional step of assessing whether the test agent has any effect on the activity or amount of one or more other such cellular components. In such a method, a test agent may be identified as a suitable CD14 antagonist antibody if it is found to decrease the activity or amount of CD14, but not to decrease, not to significantly decrease, not to significantly decrease, not to alter, or not to significantly alter, the activity or amount of one or more other cellular components, including CD14 binding partners such as MD2 and TLR4.

In the screening methods described herein, the presence of a lower CD14 agonist activity or a decreased amount of CD14 in the presence of the test agent indicates that the test agent may be a suitable antagonist antibody of CD14 for use in accordance with the present invention to treat the development or progression of a neurodegenerative disease or symptom thereof in an individual.

A test agent that is an antagonist of CD14 may result in a decrease in CD14 activity or levels of at least 5%, at least 10%, at least 25%, at least 50%, at least 60%, at least 75%, or at least 85% or more in the presence of the test agent compared to in the absence of the test agent. A test agent that is an antagonist of CD14 may result in a decrease in CD14 agonist activity or levels such that the agonist activity or level of CD14 is no longer detectable in the presence of the test agent. Such a decrease may be seen in the sample being tested or, for example where the method is carried out in an animal model, in particular tissue from the animal such as in the circulation or other organs such as the liver, kidney or heart.

A test agent that is an antagonist of CD14 is preferably a specific antagonist of CD14 as described above. However, this does not mean that a specific antagonist of CD14 has a complete absence of off-target antagonistic activity. In this regard, the specific antagonist of CD14 may have negligible or a minor direct binding and effect on other cellular components, such that the antagonism of the activity, signaling or expression of a non-CD14 cellular component, is less than less than 15%, less than 10%, less than 5%, less than 1%, or less than 0.1% of the direct binding and effect of that agent on the activity, signaling or expression of CD14.

Levels or amounts of CD14 may be measured by assessing expression of the CD14 gene. Gene expression may be assessed by looking at mRNA production or levels or at protein production or levels. Expression products such as mRNA and proteins may be identified or quantified by methods known in the art. Such methods may utilize hybridization to specifically identify the mRNA of interest. For example such methods may involve PCR or real-time PCR approaches. Methods to identify or quantify a protein of interest may involve the use of antibodies that bind that protein. For example, such methods may involve western blotting. Regulation of CD14 gene expression may be compared in the presence and absence of a test agent. Thus test agents can be identified that decrease CD14 gene expression compared to the level seen in the absence of the test agent. Such test agents may be suitable antagonists of CD14 in accordance with the invention.

The screening methods may assess the agonist activity of CD14. For example, such a method may be carried out using peripheral blood mononuclear cells. Such cells will produce cytokines such as IL-1 α, IL-6, TNF-α, IFN-β, IL-18, IL-17 and IL-8 on response to stimulation with, for example, LPS. A screening method may therefore comprise combining peripheral blood mononuclear cells with the test agent or a vehicle and adding LPS. The cells may then be incubated for an amount of time (e.g., 24 hours) to allow the production of pro-inflammatory mediators such as cytokines. The level of cytokines such as IL-la, IL-6, TNF-α, IFN-β, IL-18, IL-17 and IL-8 produced by the cells in that time period can then be assessed. If the test agent has anti-CD14 properties, then the production of such cytokines should be reduced compared to the vehicle-treated cells.

Further tests may also be carried out in order to confirm that the test agent is suitable for use in the claimed methods. For example, as explained above, a suitable antagonist antibody of CD14 should be capable of reducing the deleterious consequences of pro-inflammatory mediator production (also commonly referred to as a cytokine storm). The screening methods of the invention may therefore incorporate further steps, such as those discussed above, which involve assessing the effect of the test agent in an animal with such production of pro-inflammatory mediator (e.g., one with ALS) and comparing that effect with that seen in the absence the test agent. A suitable CD14 antagonist will be capable of ameliorating at least some of the effects of the neurodegenerative disease in the test animal.

2.3 Ancillary Anti-Neurodegenerative Agents

As indicated, compounds according to the present invention may be administered alone or in combination with other agents (also referred to herein as "ancillary anti-neurodegenerative agents"), especially including other compounds of the present invention or compounds which are not direct CD14 antagonists and are otherwise disclosed as being useful for the treatment of the development or progression of neurodegenerative diseases or symptoms thereof. For MND, including Amyotrophic Lateral Sclerosis (ALS), also known as Lou Gehrig's Disease, primary lateral sclerosis, progressive muscular atrophy, pseudobulbar palsy, progressive bulbar palsy and lower motor neurone disease, non-limiting examples of ancillary anti-neurodegenerative agents contemplated herein include Riluzole (disclosed in Miller R G et al. The Cochrane Database of Systematic Reviews. 3: CD001447); agents that block the interaction between CD40 and CD40 ligand, including antibodies that bind specifically to CD40 and/or CD40 ligand (e.g., AT-1501), and anti-inflammatories, e.g. blockers of the complement pathway, such as C5a receptor agonists (e.g. PMX205 or eculizumab (Lee J. D. et al, (2017) *British Journal of Pharmacology*, 174(8)). Non-limiting examples of other agents which may be used in combination therapy for MND include NurOwn stem cell therapy (BrainStorm Cell Therapeutics), GM604, Radicava (Radicut), Masitinib, Memantine or Tirasemtiv. For Dementia such as LBD, FTD or AD an example ancillary anti-neurodegenerative agent contemplated herein is a cholinesterase inhibitor (e.g. donepezil (Aricept), rivastigmine (Exelon) and Galantamine (Reminyl and Razadyne). Example ancillary anti-neurodegenerative agents contemplated for AD include but are not limited to an approved therapeutic selected from for example, Aricept, Razadyne, Namenda, Exelon and Namzaric. The selection of an appropriate ancillary anti-neurodegenerative agent for use in a combination therapy with a CD14 antagonist antibody as described herein would be well within the skill of the person in the art.

Ancillary anti-neurodegenerative agents may be used in combination with a CD14 antagonist antibody for their additive activity or treatment profile of neurodegenerative disease (e.g. MND and Dementia) and, in certain instances, for their synergistic effects in combination with compounds of the present invention.

When combination therapy is desired, the CD14 antagonist antibody is administered separately, simultaneously or sequentially with ancillary agent. In some embodiments, this may be achieved by administering systemically a single composition or pharmacological formulation that includes both types of agent, or by administering two separate compositions or formulations at the same time, wherein one composition includes the CD14 antagonist antibody and the other the ancillary agent. In other embodiments, the treatment with the CD14 antagonist antibody may precede or follow the treatment with the ancillary agent by intervals ranging from minutes to days.

In embodiments where the CD14 antagonist antibody is applied separately to the ancillary agent, one would generally ensure that a significant period of time did not expire between the time of each delivery, such that the CD14 antagonist antibody would still be able to exert an advantageously combined effect on inhibiting a CD14-mediated effect including inhibiting or decreasing production of pro-inflammatory mediators by peripheral cells (e.g., an immune cell such as but not limited to a macrophage, monocyte, dendritic cell or T cell) with the ancillary agent, and in particular, to maintain or enhance a subject's capacity to reverse or inhibit the development of disease or symptoms thereof.

In some situations, one may administer both modalities within about 1-12 hours of each other and, more suitably, within about 2-6 hours of each other. In some situations, it may be desirable to extend the time period for treatment significantly, however, where several hours (2, 3, 4, 5, 6 or 7) to several days (1, 2, 3, 4, 5, 6, 7 or 8) lapse between the respective administrations. In specific embodiments, the ancillary agent is administered prior to the administration of the CD14 antagonist antibody.

In embodiments where the ancillary agent is administered separately to the CD14 antagonist antibody, depending on the neurodegenerative agent and disease or symptom thereof to be treated it will be understood that the ancillary agent can be administered by a method which is different to that of the administration method used for the CD14-antagonist antibody, e.g. the ancillary agent may be administered systemically or directly to the CNS.

It is conceivable that more than one administration of either the CD14 antagonist antibody or the ancillary agent will be desired. Various combinations may be employed, where the CD14 antagonist antibody is "A" and the ancillary agent is "B", as exemplified below:

A/B/A B/A/B B/B/A A/A/B B/A/A A/B/B B/B/B/A B/B/A/B A/A/B/B A/B/A/B A/B/B/A B/B/A/A B/A/B/A B/A/A/B B/B/B/A A/A/A/B B/A/A/A A/B/A/A A/A/B/A A/B/B/B B/A/B/B B/B/A/B.

Where two or more therapeutic agents are administered to a subject "in conjunction" or "concurrently" they may be administered in a single composition at the same time, or in separate compositions at the same time, or in separate compositions separated in time.

The subject methods may also be supplemented with, or practiced in combination with, other medicinal intervention such as via a tablet, oral solution, patch or intravenous injection or other parenteral mode of administration. For example, in neurodegenerative diseases which led to diminished lung function, such as ALS, the intervention may be mechanical such as a non-invasive ventilation device or a drug may be used to ease breathing difficulties. The subject methods may also be practiced in combination with non-medical therapy, including but not limited to physical therapy, speech therapy, psychotherapy, occupational therapy.

2.4 Compositions

As described herein, the use of a CD14 antagonist antibody, whether alone or in combination with ancillary anti-neurodegenerative agents, can inhibit or decrease the production of pro-inflammatory mediators, including pro-inflammatory cytokines, from peripheral cells, by either binding cells expressing mCD14 or via binding to sCD14, and reducing the sequelae of that production, and more particularly, to treat the development or progression of neurodegenerative diseases and their symptoms.

A CD14 antagonist antibody and optionally the ancillary anti-neurodegenerative agents can be administered either by themselves or with a pharmaceutically acceptable carrier.

For use in the methods herein described, the CD14 antagonist antibodies may be formulated in a conventional manner using one or more pharmaceutically acceptable carriers, stabilizers or excipients (vehicles) to form a pharmaceutical composition as is known in the art, in particular with respect to protein active agents. Carrier(s) are "acceptable" in the sense of being compatible with the other ingredients of the composition and not deleterious to the recipient (e.g. patient) thereof. Suitable carriers typically include physiological saline or ethanol polyols such as glycerol or propylene glycol.

The antibody may be formulated as neutral or salt forms. Pharmaceutically acceptable salts include the acid addition salts (formed with free amino groups) and which are formed with inorganic acids such as hydrochloric or phosphoric acids, or such organic acids such as acetic, oxalic, tartaric and maleic. Salts formed with the free carboxyl groups may also be derived from inorganic bases such as sodium, potassium, ammonium, calcium, or ferric hydroxides, and organic bases as isopropylamine, trimethylamine, 2-ethyl-amino ethanol, histidine and procaine.

The compositions may be suitably formulated for systemic administration, including intravenous, intramuscular, subcutaneous, or intraperitoneal administration and conveniently comprise sterile aqueous solutions of the antibody, which are preferably isotonic with the blood of the recipient. Such formulations are typically prepared by dissolving solid active ingredient in water containing physiologically compatible substances such as sodium chloride, glycine, and the like, and having a buffered pH compatible with physiological conditions to produce an aqueous solution, and rendering said solution sterile. These may be prepared in unit or multi-dose containers, for example, sealed ampoules or vials.

The compositions may incorporate a stabilizer, such as for example polyethylene glycol, proteins, saccharides (for example trehalose), amino acids, inorganic acids and admixtures thereof. Stabilizers are used in aqueous solutions at the appropriate concentration and pH. The pH of the aqueous solution is adjusted to be within the range of 5.0-9.0, preferably within the range of 6-8. In formulating the antibody, anti-adsorption agent may be used. Other suitable excipients may typically include an antioxidant such as ascorbic acid. The compositions may be formulated as controlled release preparations which may be achieved through the use of polymer to complex or absorb the proteins. Appropriate polymers for controlled release formulations include for example polyester, polyamino acids, polyvinyl, pyrrolidone, ethylenevinylacetate, and methylcellulose. Another possible method for controlled release is to incorporate the antibody into particles of a polymeric material such as polyesters, polyamino acids, hydrogels, poly (lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gelatin-microcapsules and poly(methylmethacylate) microcapsules, respectively, or in colloidal drug delivery systems, for example, liposomes, albumin microspheres, microemulsions, nanoparticles, and nanocapsules or in macroemulsions.

A CD14 antagonist antibody and optionally the ancillary anti-neurodegenerative agents may also be administered directly to the airways in the form of an aerosol. For use as aerosols, the inhibitors of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

One of skill in the art will recognize that formulations are routinely designed according to their intended use, i.e. route of administration.

3. Methods of Treatment

The invention provides for therapeutic methods of treating a subject that has or is at risk of (or susceptible to) developing a neurodegenerative disease. These methods include within their scope the treatment of the development or progression of a neurodegenerative disease in humans, and animals, e.g., veterinary applications, as well as symptoms associated with such disease. Such diseases include for example, a MND selected from ALS, PLS, PMA, progressive bulbar palsy (PBP) and pseudobulbar palsy. Such diseases also include for example, a Dementia selected from Alzheimer's disease, a Lewy body dementia (DLB and PDD), Frontotemporal Dementia (FTD) and Vascular Dementia.

The present invention contemplates methods for treating the development or progression of a neurodegenerative disease or symptoms thereof in a subject by systemically administering to the subject a CD14 antagonist antibody of the invention, and optionally an ancillary anti-neurodegenerative agent. The CD14 antagonist antibody, and optionally the ancillary anti-neurodegenerative agent (also referred to herein as "therapeutic agents"), may be administered in an "effective amount (s)", to achieve an intended purpose in a subject, such as the alleviation of symptoms associated with disease. The dose of therapeutic agents(s) administered to a patient should be sufficient to achieve a beneficial response in the subject over time such as a reduction in at least one symptom associated with a neurodegenerative disease.

In an embodiment, the disease is MND and there is a reduction in at least one symptom selected from progressive muscle atrophy, paralysis, spasticity, hyperreflexia, respiratory function and other symptoms such as difficulty swallowing, limb weakness, dysarthria, slurred speech, impaired gait, facial weakness and muscle cramps. In an embodiment, the disease is Dementia and there is a reduction in at least one symptom selected from memory loss; depression, impaired communication, poor judgment, disorientation, confusion, behavior changes, movement symptoms, hallucinations, neuroleptic sensitivity and difficulty speaking, swallowing and walking.

The quantity or dose frequency of the therapeutic agent(s) to be administered may depend on the subject to be treated inclusive of the age, sex, weight and general health condition thereof. In this regard, precise amounts of the therapeutic agent(s) for administration will depend on the judgment of the practitioner. One skilled in the art would be able, by routine experimentation, to determine an effective, non-toxic amount of a CD14 antagonist antibody, and optionally an ancillary anti-neurodegenerative agent described herein, to include in a pharmaceutical composition of the present invention for the desired therapeutic outcome.

In some embodiments, an "effective amount" of a therapeutic agent is an amount wherein the active ingredients are contained in an amount effective to achieve the intended purpose. More specifically, a therapeutically effective amount means an amount of active ingredients (CD14 antagonist) effective to inhibit or decrease the production of one or more pro-inflammatory mediators to treat symptoms of a neurodegenerative disease (e.g., ALS or AD) to prolong the survival of the subject being treated. Determination of a therapeutically effective amount is well within the capability of those skilled in the art, especially in light of the detailed disclosure provided herein.

Subjects with a neurodegenerative disease or at risk for a neurodegenerative disease include patients who have one or more biomarkers of disease severity, or which indicate a susceptibility to developing a neurodegenerative disease. In an embodiment the disease is MND and the biomarkers are selected from one or more of e.g. SOD1, TDP-43, FUS, C9ORF72, ALS2, ALS4, ALS8, NEK1, UBQLN2, VCP, SETX, ANG, PFN1, MATR3, CHCHD10, TUBA4A, TBK1, C21orf2 and OPTN or an expression product thereof. In this embodiment, the presence of a marker of a neurodegenerative disease is suitably determined by detecting presence or overexpression of an expression product of a marker gene and/or presence of a mutation in a marker gene (e.g., SOD1, TDP-43, FUS, C9ORF72, ALS2, ALS4, ALS8, NEK1, UBQLN2, VCP, SETX, ANG, PFN1, MATR3, CHCHD10, TUBA4A, TBK1, C21orf2 and OPTN mRNA or polypeptide) in the biological sample. In some embodiments for MND, the presence of cytoplasmic deposition of TDP-43-positive inclusions and/or elevated serum and/or CSF levels of neurofilaments, may also be determined.

In another embodiment, the disease is Dementia including Alzheimer's disease, FTD the LBD's (DLB and PDD) and Vascular Dementia and the marker is selected from one or more of a mutation in the gene encoding amyloid precursor protein (APP) and presenilins 1 and 2, mutations in the ε4, 2 and 3 alleles of the apolipoprotein E (APOE) gene (APOE-ε4, APOE-ε2, APOE-ε3), mutations in Triggering receptor expressed on myeloid cells 2 (TREM2) gene, MAPT gene, GRN gene, also called the PGRN gene, TAR-DBP gene, VCP gene and the CHMP2B gene. Elevated serum and/or CSF levels of α-synuclein, S100A9 and S100B, chromogranin, circulating DNA, heat shock proteins and amyloid may also be determined.

In other embodiments, subjects at risk for a neurodegenerative disease may also be identified by determining the presence of elevated levels of one or more of pro-inflammatory cytokines associated with disease, e.g. TNF, IL-1-α, IL-6, IFN-8, IL-18, IL-8, IL-18, C-reactive protein (CRP), IL-17, chemokines, CD14+-high monocytes and inflammatory mediator mRNA transcripts in peripheral blood mononuclear cells (PBMC). In an embodiment, the disease is MND and the cytokine is selected from one or more of IL-6 or IL-17. In an embodiment, the disease is Dementia and the cytokine is selected from IL-1, IL-6 and TNF-α.

It will be understood that any known biomarker of a neurodegenerative disease may be used to identify subjects who have disease or are at risk of disease.

Administration of a prophylactic agent can occur prior to the manifestation of symptoms characteristic of a neurodegenerative disease, such that a disease is inhibited or, alternatively, delayed in its progression.

In order that the invention may be readily understood and put into practical effect, particular preferred embodiments will now be described by way of the following non-limiting example.

EXAMPLES

Example 1

Treatment and Prophylaxis of Patients with MND by Systemically Administering Monoclonal Antibody IC14
Experimental Design patients with familial or sporadic MND (defined as clinically possible, probable, or definite by Awaji-Shima Consensus Recommendations), who exhibited their first symptoms of MND within 3 years of informed consent and who are aged between 18 and 75 years, will be recruited.

Dosage Regimen

Patients will be assigned to receive one of two dose regimens of IC14 in an unblinded manner: all doses will be delivered IV as an infusion over a 2-hour period:

For the initial 3 patients: IC14 at a dosage of 2 mg/kg on Study Day 1, then 1 mg/kg once daily on Study Days 3-5 for 4 total doses.

For the subsequent 7 patients: IC14 at a dosage of 4 mg/kg on Study Day 1, then 2 mg/kg once daily on Study Days 2-4 for 4 total doses.

Study participation will continue until 28 days after the last dose of study drug.

Dosage Form:

Sterile glass vial containing IC14, 5 mg/mL in a 30-mL vial (125 mg in 25 mL delivered). Study drug will be prepared in 250 mL sterile normal saline for injection to be infused over two hours intravenously.

Study Endpoints:

The primary endpoint of the study is safety, tolerability and lack of immunogenicity of IC14. Safety and tolerability of IC14 will be determined by examining the toxicities and adverse events that are attributable to treatment. Safety parameters will include an evaluation of the clinical signs and symptoms from the history and physical exam, vital signs, adverse events, and laboratory findings (Chem-20, CBC, platelet count, coagulation studies). Immunogenicity studies will measure antibodies against IC14.

The secondary endpoints are:

Peak serum IC14 concentration following administration of the initial dose, peak serum and cerebrospinal fluid (CSF) concentrations following a course of treatment and area under the serum IC14 concentration versus time curve (AUC) following administration of the initial dose and following a course of treatment.

Treatment-related changes in disease severity by the Revised Amyotrophic Lateral Sclerosis Functional Rating Scale (ALSFRS-R), in respiratory function by seated forced vital capacity (FVC) and other RFT parameters and by sniff nasal pressure (SNP) test.

Treatment-related change in quality of life by the ALS Specific Quality of Life-Revised (ALSSQOL-R) score and in cognitive function by Edinburgh Cognitive and Behavioural Assessment (ECAS) score.

Treatment-related change in disease biomarker profiles, to include CRP, IL-6, IL-17, IL-1B and neurofilament heavy and light chains.

Sample Collection and Patient Evaluation:

Samples will be collected from patients as detailed in Table 2:

TABLE 2

SAMPLE COLLECTION

| Procedure | Patients 1-3 | Patients 4-10 |
|---|---|---|
| Lumbar puncture for biomarker analysis, pharmacokinetics | Baseline, days 5, 8 | Baseline, days 4, 8 |
| Serum for pharmacokinetics | Baseline, days 1, 2, 5, 6, 8 | Baseline, days 1, 2, 4, 5, 8 |
| Serum for sCD14/sCD14-ST, whole blood for CD14 receptor saturation | Baseline, days 1, 5 | Baseline, days 1, 4 |
| Serum for biomarker analysis | Baseline, days 5, 33 | Baseline, days 4, 32 |
| Serum for anti-IC14 antibody titer | Baseline, day 33 | Baseline, day 32 |
| Blood for hematology, chemistry and coagulation analysis | Screening, baseline, days 2, 5, 15, 22, 33 | Screening, baseline, days 2, 4, 15, 22, 32 |

TABLE 2-continued

SAMPLE COLLECTION

| Procedure | Patients 1-3 | Patients 4-10 |
|---|---|---|
| ALSFRS-R Assessment, completion of ALSSQOL-R Questionnaire and ECAS Questionnaire | Baseline, day 33 | Baseline, day 32 |
| RFTs, including seated FVC and sniff nasal pressure test | Screening, days 5 and 33 | Screening, days 4 and 32 |
| Slit lamp exam | Screening, day 33 | Screening, day 32 |

Data Analysis

MND biomarkers will be measured, including plasma concentrations of transactive response element (TAR)-DNA binding protein (TDP)-43 and neurofilaments. Serum and CSF neurofilaments may be evaluated.

Other potential biomarkers of which one or more will be evaluated include CRP, SOD1, IL-1β, IL-6, IL-17, chemokines, CD14+-high monocytes and inflammatory mediator mRNA transcripts in peripheral blood mononuclear cells (PBMC). Serum and CSF will be evaluated in vitro for ability to inhibit inflammatory gene activation.

Pharmacodynamic evaluations will be done by measuring the saturation of CD14 on monocytes and levels of circulating sCD14 at baseline and immediately following dose 1 and dose 4 of study drug. Pharmacokinetic measurements of IC14 in serum will be done at baseline; immediately after and 6 and 22 hours after dose 1; before and immediately after and 24 hours after dose 4; and washout. Pharmacokinetic measurements of IC14 in CSF will be done at baseline, after the fourth dose of IC14 and during washout.

Study participation will continue until 28 days after the last dose of study drug. Study participation will be for a total of 32-33 days plus up to 4 weeks for screening evaluations.

Study Days are defined as consecutive calendar days beginning from the start time of the first study drug administration (Study Day 1). Study drug will be administered at approximately 24-hr intervals (or a 48-hour interval between the first and second dose for the first three patients dosed) beginning from the start time of the first study drug administration (Study Day 1).

Information will be collected on the pharmacokinetics and pharmacodynamics of IC14 in blood and CSF of MND patients, to include:

Baseline, peak and washout serum IC14 concentration following administration of the initial dose and baseline, peak and washout serum and cerebrospinal fluid (CSF) concentrations following a course of treatment.

Area-under-the-serum-IC14-concentration versus time curve (AUC) following administration of the initial dose and following a course of treatment.

Circulating monocyte CD14 receptor binding and sCD14±sCD14-ST (presepsin) levels will be calculated at baseline, and after Dose 1 and Dose 4.

Information on treatment-related changes in disease biomarker profiles in peripheral blood and CSF, to include immune cells, levels of inflammatory cytokines and chemokines and changes in other biomarkers including neurofilament (NF) heavy and light chain levels.

Compound

The study drug, IC14, will be supplied by Implicit Bioscience Ltd. (Queensland, Australia). IC14 is a recombinant chimeric (murine/human) monoclonal antibody against human CD14. The murine parent is an antibody designated 28C5. IC14 is secreted from Chinese hamster ovary cells as an L2H2γ4 immunoglobulin.

Results

Results were obtained for a single patient who had received the full dose of IC14, i.e. a dosage of 4 mg/kg on Study Day 1, then 2 mg/kg once daily on Study Days 2-4 for 4 total doses. As described above, lumbar punctures were performed at baseline and on Study Days 4 and 8 and CSF collected. Levels of IL-17 and IL-113 were measured by multiplex analysis and levels of neurofilament light chain (NFL) were measured by ELISA. As shown in FIG. 1, treatment with IC14 resulted in a decrease in levels of the inflammatory markers IL-17 and IL-113 in the CSF at day 8, and also a decrease in NFL, which is a marker of disease. IL-17 and IL-113 have been associated with disease both in ALS/MND patients and in ALS/MND disease models (Rentzos et al. (2010) Acta Neurol. Scand. 122, 425-9; Fiala et al. (2010) Neuroinflammation 7, 76; Meissner et al. (2010) Proc. Natl. Acad. Sci. 107, 13046-13050; van der Meer & Simon. (2010) Proc. Natl. Acad. Sci. U.S.A 107, 12741-2; and Zhao et al. (2015) Exp. Neurol. 273, 24-35), whilst NFL has been described as a marker of neurodegeneration. The ability of IC14 to modulate the levels of these molecules in the CSF when delivered systemically to a subject with MND indicates that intravenous IC14 treatment has therapeutic utility in curbing neuroinflammatory processes driving ALS/MND.

Example 2

IC14 Inhibition of TDP-43-Driven Activation of Primary Human Microglial Cells

Immune responses in the brain and spinal cord are primarily mediated by microglia which act as a first line of defense and play a key role in initiating and sustaining neuro-inflammatory responses driving neurodegenerative diseases, including ALS (Salter & Stevens (2017) Nat. Med. 23, 1018-1027).

SOD1 and TDP-43 are intracellular proteins that have been implicated in ALS. In vitro systems using mouse microglia have demonstrated that both proteins are able to act as Damage-Associated Molecular Patterns (DAMPS), activating microglial cells, inducing pro-inflammatory cytokines and promoting neurotoxicity. These responses utilize TLR and NLRP3 signaling, with DAMP-driven activation is inhibited by blocking antibodies to TLR2, TLR4 or CD14 (Zhao et al. (2010) Glia 58, 231-243; and Zhao et al. (2015) Exp. Neurol. 273, 24-35), pointing to a role for the blockade of CD14 in the inhibition of neuroinflammation.

A tissue culture system for the growth of primary human microglial cells was used to determine if the DAMP TDP-43 activates human microglial cells, so as to identify inflammatory readouts of this activation process and to evaluate the ability of IC14 to inhibit this activation.

Materials and Methods
Reagents

IC14 was provided by Implicit Bioscience Ltd (IC14-3, Lot 1-FIN-0779), and the activity and stability of this GMP antibody was confirmed by stability testing. As a control for IC14, the isotype control human IgG4 antibody was obtained from Australian Biosearch (Ultra-LEAF™ Purified Human IgG4 Isotype, catalog #403402).

Recombinant TDP-43 produced in E. coli in both wild-type and mutant (Q331K) forms was provided by Associate Professor Julie Atkins, Macquarie University.

Microglial Cell Culture

Primary human microglial cultures were established using a modification of the protocol described by Guillemin et al. (J. Neurosci. Res. (1997) 49, 576-591). Briefly, fetal human brain tissue was collected from 14 to 19 weeks old aborted fetuses collected after therapeutic termination after obtaining informed consent (approved by the Human Research Ethics Committee of Macquarie University; HREC 5201600719). One gram of this material was divided equally by surgical dissection amongst 24 wells of a 24 well tissue culture plate (Corning) and cultured for 5 days in DMEM with 10% heat inactivated fetal calf serum (FCS) at 37° C. in 5% $CO_2$. Non-microglial cells were removed by a 2 minute trypsinization step, followed by neutralization with DMEM plus FCS, leaving the microglia cells adhering to the plate. Microglia were cultured for an additional 48 hrs before treatment.

Microglial Stimulation

One-week old primary microglial cultures were pre-treated with either IC14 or a control IgG4 mAb antibody at the following concentrations for 2 hours: Untreated; IC14 at a final concentration of 14/ml, 10 ng/ml or 10 ng/ml; Control IgG4 at a final concentration of 14/ml, 10 ng/ml, or 10 ng/ml.

Wild-type or mutant TDP-43 was then added to a final concentration of 500 ng/ml. Control wells received no TDP-43.

Cultures were incubated in DMEM with 10% heat inactivated FCS at 37° C. in 5% $CO_2$ for 48 hours. Supernatants were collected for multiplex cytokine analysis and analyzed in triplicate using a 65-plex cytokine and chemokine array (Human Cytokine/Chemokine 65-Plex Panel, Eve Technologies, Calgary, Alberta) and for profiling of kynurenine pathway metabolites.

Results

Cytokine/Chemokine Induction

Figure 2B:
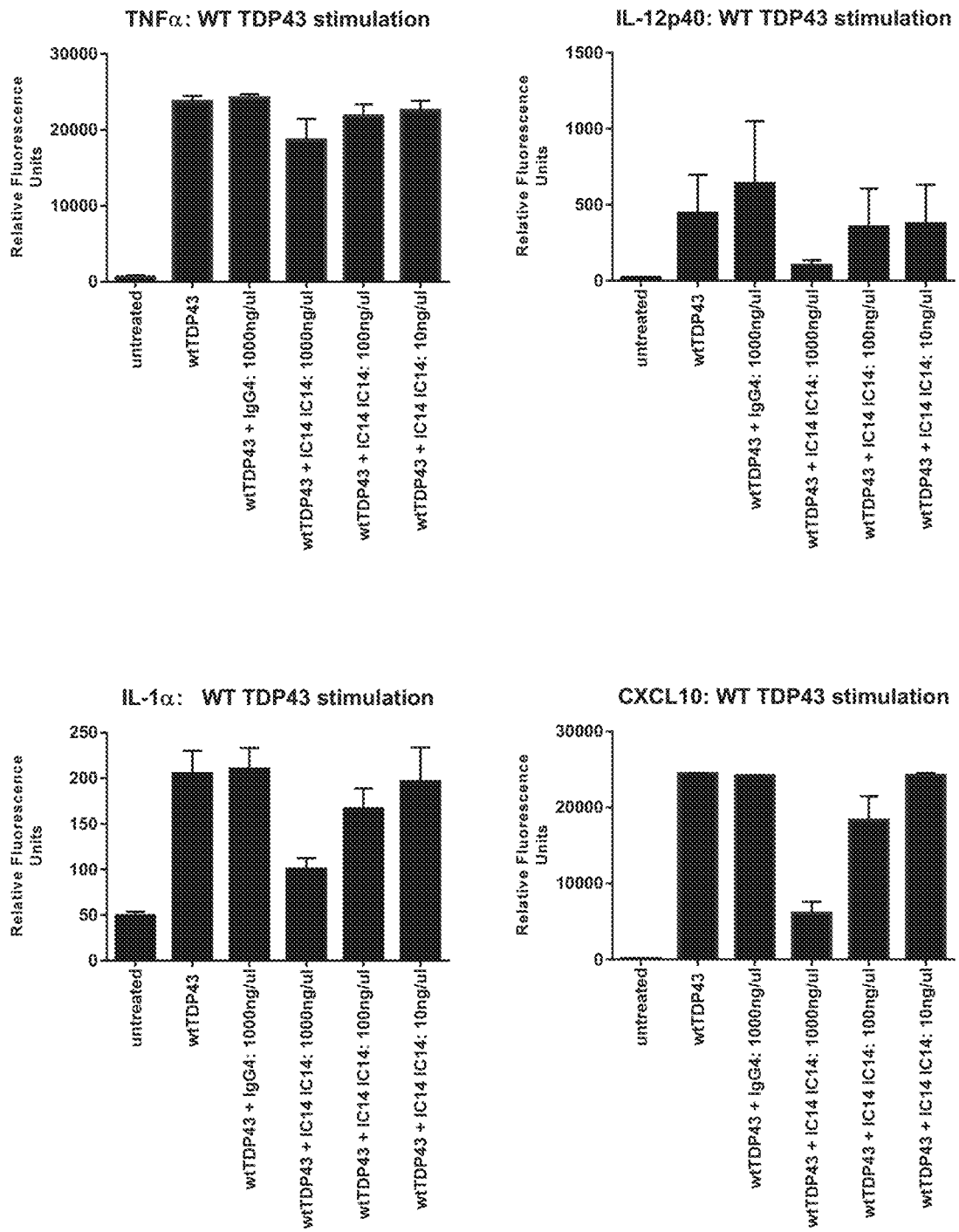

In the absence of any external stimulation primary human microglia produced a range of cytokines and chemokines, including many which have been identified in the circulation or in the CSF of patients with ALS (FIGS. 2A-2B). The majority of these molecules were expressed at low levels, but showed significant upregulation when stimulated with either wild-type or mutant TDP-43 (Q331K), a protein which has been shown to be mutated in patients with both familial and sporadic MND, and which has been described as having proinflammatory properties (Zhao et al. (2015) Exp. Neurol. 273, 24-35). Minimal differences were detected in the ability of wild-type or mutant TDP-43 to activate microglial cells, in agreement with the observations of Zhao et al. The cytokines and chemokines produced include the proinflammatory cytokines TNFα, $IL1_\alpha$ and IL-12p40, as well as the chemokines CXCL10, and CCL5 which play a role in promoting the recruitment of inflammatory cells to sites of inflammation (FIGS. 2A and 2B). TDP-43 may thus be initiating and sustaining motor neurone damage in ALS by the activation of microglia, the localized production of inflammatory mediators and the subsequent recruitment of inflammatory cells to sites of neuronal damage.

Pretreatment of microglial cultures with an isotype control antibody had no effect on this TDP-43-driven cytokine production. The inclusion of IC14 resulted in a dose-dependent inhibition of both wild-type and mutant TDP-43-driven cytokine and chemokine production, including an inhibition of TNFα, IL-1α, IL12p40 and CXCL10 (FIGS. 2A and 2B). For a number of these analytes expression levels after TDP-43 stimulation were elevated beyond the range of the standard curve (e.g. TNFα, CXCL10) which precluded an exact characterization of expression levels. Nevertheless, inhibition of cytokine or chemokine production was detected under these extreme conditions, suggesting that IC14 may be efficacious in in vitro assays utilizing more physiological DAMP-driven stimulatory conditions.

The disclosure of every patent, patent application, and publication cited herein is hereby incorporated herein by reference in its entirety.

The citation of any reference herein should not be construed as an admission that such reference is available as "Prior Art" to the instant application.

Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appended claims.

What is claimed is:

1. A method for treating the development or progression of amyotrophic lateral sclerosis (ALS) or a symptom thereof in a subject, the method comprising administering systemically an effective amount of a CD14 antagonist antibody to the subject, wherein the CD14 antagonist antibody comprises a VL domain and a VH domain, wherein:

the VL domain comprises a L-CDR1, a L-CDR2 and a L-CDR3 within the sequence set forth in SEQ ID NO:25; and the VH domain comprises a H-CDR1, a H-CDR2 and a H-CDR3 within the sequence set forth in SEQ ID NO:26.

2. The method of claim 1, wherein:

the VL domain comprises the VL domain within the amino acid sequence set forth in SEQ ID NO: 25; and the VH domain comprises the VH domain within the amino acid sequence set forth in SEQ ID NO: 26.

3. The method of claim 1, wherein the CD14 antagonist antibody comprises a light chain and a heavy chain, wherein:

the light chain comprises the amino acid sequence set forth in SEQ ID NO: 25; and the heavy chain comprises the amino acid sequence set forth in SEQ ID NO: 26.

4. The method of claim 1, wherein the CD14 antagonist antibody is IC14, or an antigen-binding fragment thereof.

5. The method of claim 1, wherein the CD14 antagonist antibody is administered in combination with one or more ancillary agents that treat the ALS or symptom thereof.

6. The method of claim 5, wherein the ancillary agent is selected from the group consisting of riluzole, edaravone, PMX205, eculizumab, and AT-501.

* * * * *

SEQUENCE LISTING

```
<160> NUMBER OF SEQ ID NOS: 26

<210> SEQ ID NO 1
<211> LENGTH: 106
<212> TYPE: PRT
<213> ORGANISM: Artificial sequence
<220> FEATURE:
<223> OTHER INFORMATION: Humanised VL domain

<400> SEQUENCE: 1

Gln Ser Pro Ala Ser Leu Ala Val Ser Leu Gly Gln Arg Ala Thr Ile
1               5                   10                  15

Ser Cys Arg Ala Ser Glu Ser Val Asp Ser Phe Gly Asn Ser Phe Met
```

```
                20                  25                  30
His Trp Tyr Gln Gln Lys Ala Gly Gln Pro Lys Ser Ser Ile Tyr
            35                  40                  45

Arg Ala Ala Asn Leu Glu Ser Gly Ile Pro Ala Arg Phe Ser Gly Ser
 50                  55                  60

Gly Ser Arg Thr Asp Phe Thr Leu Thr Ile Asn Pro Val Glu Ala Asp
 65                  70                  75                  80

Asp Val Ala Thr Tyr Phe Cys Gln Gln Ser Tyr Glu Asp Pro Trp Thr
                 85                  90                  95

Phe Gly Gly Gly Thr Lys Leu Gly Asn Gln
                100                 105
```

<210> SEQ ID NO 2
<211> LENGTH: 105
<212> TYPE: PRT
<213> ORGANISM: Artificial sequence
<220> FEATURE:
<223> OTHER INFORMATION: Humanised VH domain

<400> SEQUENCE: 2

```
Leu Val Lys Pro Gly Gly Ser Leu Lys Leu Ser Cys Val Ala Ser Gly
 1               5                  10                  15

Phe Thr Phe Ser Ser Tyr Ala Met Ser Trp Val Arg Gln Thr Pro Glu
                20                  25                  30

Lys Arg Leu Glu Trp Val Ala Ser Ile Ser Ser Gly Gly Thr Thr Tyr
                35                  40                  45

Tyr Pro Asp Asn Val Lys Gly Arg Phe Thr Ile Ser Arg Asp Asn Ala
 50                  55                  60

Arg Asn Ile Leu Tyr Leu Gln Met Ser Ser Leu Arg Ser Glu Asp Thr
 65                  70                  75                  80

Ala Met Tyr Tyr Cys Ala Arg Gly Tyr Tyr Asp Tyr His Tyr Trp Gly
                 85                  90                  95

Gln Gly Thr Thr Leu Thr Val Ser Ser
                100                 105
```

<210> SEQ ID NO 3
<211> LENGTH: 106
<212> TYPE: PRT
<213> ORGANISM: Artificial sequence
<220> FEATURE:
<223> OTHER INFORMATION: Humanised VL domain

<400> SEQUENCE: 3

```
Gln Ser Pro Ala Ser Leu Ala Val Ser Leu Gly Gln Arg Ala Thr Ile
 1               5                  10                  15

Ser Cys Arg Ala Ser Glu Ser Val Asp Ser Tyr Val Asn Ser Phe Leu
                20                  25                  30

His Trp Tyr Gln Gln Lys Pro Gly Gln Pro Pro Lys Leu Leu Ile Tyr
                35                  40                  45

Arg Ala Ser Asn Leu Gln Ser Gly Ile Pro Ala Arg Phe Ser Gly Ser
 50                  55                  60

Gly Ser Arg Thr Asp Phe Thr Leu Thr Ile Asn Pro Val Glu Ala Asp
 65                  70                  75                  80

Asp Val Ala Thr Tyr Cys Cys Gln Gln Ser Asn Glu Asp Pro Thr Thr
                 85                  90                  95

Phe Gly Gly Gly Thr Lys Leu Glu Ile Lys
                100                 105
```

<210> SEQ ID NO 4
<211> LENGTH: 112
<212> TYPE: PRT
<213> ORGANISM: Artificial sequence
<220> FEATURE:
<223> OTHER INFORMATION: Humanised VH domain

<400> SEQUENCE: 4

```
Leu Gln Gln Ser Gly Pro Gly Leu Val Lys Pro Ser Gln Ser Leu Ser
1               5                   10                  15
Leu Thr Cys Thr Val Thr Gly Tyr Ser Ile Thr Ser Asp Ser Ala Trp
            20                  25                  30
Asn Trp Ile Arg Gln Phe Pro Gly Asn Arg Leu Glu Trp Met Gly Tyr
        35                  40                  45
Ile Ser Tyr Ser Gly Ser Thr Ser Tyr Asn Pro Ser Leu Lys Ser Arg
50                  55                  60
Ile Ser Ile Thr Arg Asp Thr Ser Lys Asn Gln Phe Phe Leu Gln Leu
65                  70                  75                  80
Asn Ser Val Thr Thr Glu Asp Thr Ala Thr Tyr Tyr Cys Val Arg Gly
                85                  90                  95
Leu Arg Phe Ala Tyr Trp Gly Gln Gly Thr Leu Val Thr Val Ser Ala
            100                 105                 110
```

<210> SEQ ID NO 5
<211> LENGTH: 101
<212> TYPE: PRT
<213> ORGANISM: Artificial sequence
<220> FEATURE:
<223> OTHER INFORMATION: Humanised VL domain

<400> SEQUENCE: 5

```
Gln Thr Pro Ser Ser Leu Ser Ala Ser Leu Gly Asp Arg Val Thr Ile
1               5                   10                  15
Ser Cys Arg Ala Ser Gln Asp Ile Lys Asn Tyr Leu Asn Trp Tyr Gln
            20                  25                  30
Gln Pro Gly Gly Thr Val Lys Val Leu Ile Tyr Tyr Thr Ser Arg Leu
        35                  40                  45
His Ser Gly Val Pro Ser Arg Phe Ser Gly Ser Gly Ser Gly Thr Asp
50                  55                  60
Tyr Ser Leu Thr Ile Ser Asn Leu Glu Gln Glu Asp Phe Ala Thr Tyr
65                  70                  75                  80
Phe Cys Gln Arg Gly Asp Thr Leu Pro Trp Thr Phe Gly Gly Gly Thr
                85                  90                  95
Lys Leu Glu Ile Lys
            100
```

<210> SEQ ID NO 6
<211> LENGTH: 116
<212> TYPE: PRT
<213> ORGANISM: Artificial sequence
<220> FEATURE:
<223> OTHER INFORMATION: Humanised VH domain

<400> SEQUENCE: 6

```
Leu Glu Ser Gly Pro Gly Leu Val Ala Pro Ser Gln Ser Leu Ser Ile
1               5                   10                  15
Thr Cys Thr Val Ser Gly Phe Ser Leu Thr Asn Tyr Asp Ile Ser Trp
            20                  25                  30
Ile Arg Gln Pro Pro Gly Lys Gly Leu Glu Trp Leu Gly Val Ile Trp
```

```
                35                  40                  45
Thr Ser Gly Gly Thr Asn Tyr Asn Ser Ala Phe Met Ser Arg Leu Ser
         50                  55                  60

Ile Thr Lys Asp Asn Ser Glu Ser Gln Val Phe Leu Lys Met Asn Gly
 65                  70                  75                  80

Leu Gln Thr Asp Asp Thr Gly Ile Tyr Tyr Cys Val Arg Gly Asp Gly
                 85                  90                  95

Asn Phe Tyr Leu Tyr Asn Phe Asp Tyr Trp Gly Gln Gly Thr Thr Leu
            100                 105                 110

Thr Val Ser Ser
        115

<210> SEQ ID NO 7
<211> LENGTH: 15
<212> TYPE: PRT
<213> ORGANISM: Artificial sequence
<220> FEATURE:
<223> OTHER INFORMATION: Humanised CDR1

<400> SEQUENCE: 7

Arg Ala Ser Glu Ser Val Asp Ser Phe Gly Asn Ser Phe Met His
 1               5                  10                  15

<210> SEQ ID NO 8
<211> LENGTH: 7
<212> TYPE: PRT
<213> ORGANISM: Artificial sequence
<220> FEATURE:
<223> OTHER INFORMATION: Humanised L-CDR2

<400> SEQUENCE: 8

Arg Ala Ala Asn Leu Glu Ser
 1               5

<210> SEQ ID NO 9
<211> LENGTH: 9
<212> TYPE: PRT
<213> ORGANISM: Artificial sequence
<220> FEATURE:
<223> OTHER INFORMATION: Humanised L-CDR3

<400> SEQUENCE: 9

Gln Gln Ser Tyr Glu Asp Pro Trp Thr
 1               5

<210> SEQ ID NO 10
<211> LENGTH: 5
<212> TYPE: PRT
<213> ORGANISM: Artificial sequence
<220> FEATURE:
<223> OTHER INFORMATION: Humanised H-CDR1

<400> SEQUENCE: 10

Ser Tyr Ala Met Ser
 1               5

<210> SEQ ID NO 11
<211> LENGTH: 16
<212> TYPE: PRT
<213> ORGANISM: Artificial sequence
<220> FEATURE:
<223> OTHER INFORMATION: Humanised H-CDR2

<400> SEQUENCE: 11
```

```
Ser Ile Ser Ser Gly Gly Thr Thr Tyr Tyr Pro Asp Asn Val Lys Gly
1               5                   10                  15
```

<210> SEQ ID NO 12
<211> LENGTH: 7
<212> TYPE: PRT
<213> ORGANISM: Artificial sequence
<220> FEATURE:
<223> OTHER INFORMATION: Humanised H-CDR3

<400> SEQUENCE: 12

```
Gly Tyr Tyr Asp Tyr His Tyr
1               5
```

<210> SEQ ID NO 13
<211> LENGTH: 15
<212> TYPE: PRT
<213> ORGANISM: Artificial sequence
<220> FEATURE:
<223> OTHER INFORMATION: Humanised L-CDR1

<400> SEQUENCE: 13

```
Arg Ala Ser Glu Ser Val Asp Ser Tyr Val Asn Ser Phe Leu His
1               5                   10                  15
```

<210> SEQ ID NO 14
<211> LENGTH: 7
<212> TYPE: PRT
<213> ORGANISM: Artificial sequence
<220> FEATURE:
<223> OTHER INFORMATION: Humanised L-CDR2

<400> SEQUENCE: 14

```
Arg Ala Ser Asn Leu Gln Ser
1               5
```

<210> SEQ ID NO 15
<211> LENGTH: 9
<212> TYPE: PRT
<213> ORGANISM: Artificial sequence
<220> FEATURE:
<223> OTHER INFORMATION: Humanised L-CDR3

<400> SEQUENCE: 15

```
Gln Gln Ser Asn Glu Asp Pro Thr Thr
1               5
```

<210> SEQ ID NO 16
<211> LENGTH: 6
<212> TYPE: PRT
<213> ORGANISM: Artificial sequence
<220> FEATURE:
<223> OTHER INFORMATION: Humanised H-CDR1

<400> SEQUENCE: 16

```
Ser Asp Ser Ala Trp Asn
1               5
```

<210> SEQ ID NO 17
<211> LENGTH: 16
<212> TYPE: PRT
<213> ORGANISM: Artificial sequence
<220> FEATURE:
<223> OTHER INFORMATION: Humanised H-CDR2

<400> SEQUENCE: 17

```
Tyr Ile Ser Tyr Ser Gly Ser Thr Ser Tyr Asn Pro Ser Leu Lys Ser
1               5                   10                  15
```

<210> SEQ ID NO 18
<211> LENGTH: 6
<212> TYPE: PRT
<213> ORGANISM: Artificial sequence
<220> FEATURE:
<223> OTHER INFORMATION: Humanised H-CDR3

<400> SEQUENCE: 18

Gly Leu Arg Phe Ala Tyr
1               5

<210> SEQ ID NO 19
<211> LENGTH: 11
<212> TYPE: PRT
<213> ORGANISM: Artificial sequence
<220> FEATURE:
<223> OTHER INFORMATION: Humanised L-CDR1

<400> SEQUENCE: 19

Arg Ala Ser Gln Asp Ile Lys Asn Tyr Leu Asn
1               5                   10

<210> SEQ ID NO 20
<211> LENGTH: 7
<212> TYPE: PRT
<213> ORGANISM: Artificial sequence
<220> FEATURE:
<223> OTHER INFORMATION: Humanised L-CDR2

<400> SEQUENCE: 20

Tyr Thr Ser Arg Leu His Ser
1               5

<210> SEQ ID NO 21
<211> LENGTH: 9
<212> TYPE: PRT
<213> ORGANISM: Artificial sequence
<220> FEATURE:
<223> OTHER INFORMATION: Humanised L-CDR3

<400> SEQUENCE: 21

Gln Arg Gly Asp Thr Leu Pro Trp Thr
1               5

<210> SEQ ID NO 22
<211> LENGTH: 5
<212> TYPE: PRT
<213> ORGANISM: Artificial sequence
<220> FEATURE:
<223> OTHER INFORMATION: Humanised H-CDR1

<400> SEQUENCE: 22

Asn Tyr Asp Ile Ser
1               5

<210> SEQ ID NO 23
<211> LENGTH: 16
<212> TYPE: PRT
<213> ORGANISM: Artificial sequence
<220> FEATURE:
<223> OTHER INFORMATION: Humanised H-CDR2

<400> SEQUENCE: 23

Val Ile Trp Thr Ser Gly Gly Thr Asn Tyr Asn Ser Ala Phe Met Ser
1               5                   10                  15

```
<210> SEQ ID NO 24
<211> LENGTH: 12
<212> TYPE: PRT
<213> ORGANISM: Artificial sequence
<220> FEATURE:
<223> OTHER INFORMATION: Humanised H-CDR3

<400> SEQUENCE: 24

Gly Asp Gly Asn Phe Tyr Leu Tyr Asn Phe Asp Tyr
1               5                   10

<210> SEQ ID NO 25
<211> LENGTH: 238
<212> TYPE: PRT
<213> ORGANISM: Artificial sequence
<220> FEATURE:
<223> OTHER INFORMATION: Humanised VL domain

<400> SEQUENCE: 25

Met Glu Thr Asp Thr Ile Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Cys Arg Ala Ser Glu Ser
        35                  40                  45

Val Asp Ser Tyr Val Asn Ser Phe Leu His Trp Tyr Gln Gln Lys Pro
    50                  55                  60

Gly Gln Pro Pro Lys Leu Leu Ile Tyr Arg Ala Ser Asn Leu Gln Ser
65                  70                  75                  80

Gly Ile Pro Ala Arg Phe Ser Gly Ser Gly Ser Arg Thr Asp Phe Thr
                85                  90                  95

Leu Thr Ile Asn Pro Val Glu Ala Asp Asp Val Ala Thr Tyr Tyr Cys
            100                 105                 110

Gln Gln Ser Asn Glu Asp Pro Tyr Thr Phe Gly Gly Gly Thr Lys Leu
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 26
<211> LENGTH: 460
<212> TYPE: PRT
<213> ORGANISM: Artificial sequence
<220> FEATURE:
<223> OTHER INFORMATION: Humanised VH domain

<400> SEQUENCE: 26
```

```
Met Lys Val Leu Ser Leu Leu Tyr Leu Leu Thr Ala Ile Pro Gly Ile
1               5                   10                  15

Leu Ser Asp Val Gln Leu Gln Gln Ser Gly Pro Gly Leu Val Lys Pro
            20                  25                  30

Ser Gln Ser Leu Ser Leu Thr Cys Thr Val Thr Gly Tyr Ser Ile Thr
        35                  40                  45

Ser Asp Ser Ala Trp Asn Trp Ile Arg Gln Phe Pro Gly Asn Arg Leu
    50                  55                  60

Glu Trp Met Gly Tyr Ile Ser Tyr Ser Gly Thr Ser Tyr Asn Pro
65                  70                  75                  80

Ser Leu Lys Ser Arg Ile Ser Ile Thr Arg Asp Thr Ser Lys Asn Gln
                85                  90                  95

Phe Phe Leu Gln Leu Asn Ser Val Thr Thr Glu Asp Thr Ala Thr Tyr
            100                 105                 110

Tyr Cys Val Arg Gly Leu Arg Phe Ala Tyr Trp Gly Gln Gly Thr Leu
        115                 120                 125

Val Thr Val Ser Ser Ala Ser Thr Lys Gly Pro Ser Val Phe Pro Leu
    130                 135                 140

Ala Pro Cys Ser Arg Ser Thr Ser Glu Ser Thr Ala Ala Leu Gly Cys
145                 150                 155                 160

Leu Val Lys Asp Tyr Phe Pro Glu Pro Val Thr Val Ser Trp Asn Ser
                165                 170                 175

Gly Ala Leu Thr Ser Gly Val His Thr Phe Pro Ala Val Leu Gln Ser
            180                 185                 190

Ser Gly Leu Tyr Ser Leu Ser Ser Val Val Thr Val Pro Ser Ser Ser
        195                 200                 205

Leu Gly Thr Lys Thr Tyr Thr Cys Asn Val Asp His Lys Pro Ser Asn
210                 215                 220

Thr Lys Val Asp Lys Arg Val Glu Ser Lys Tyr Gly Pro Pro Cys Pro
225                 230                 235                 240

Ser Cys Pro Ala Pro Glu Phe Leu Gly Gly Pro Ser Val Phe Leu Phe
            245                 250                 255

Pro Pro Lys Pro Lys Asp Thr Leu Met Ile Ser Arg Thr Pro Glu Val
            260                 265                 270

Thr Cys Val Val Val Asp Val Ser Gln Glu Asp Pro Glu Val Gln Phe
    275                 280                 285

Asn Trp Tyr Val Asp Gly Val Glu Val His Asn Ala Lys Thr Lys Pro
290                 295                 300

Arg Glu Glu Gln Phe Asn Ser Thr Tyr Arg Val Val Ser Val Leu Thr
305                 310                 315                 320

Val Leu His Gln Asp Trp Leu Asn Gly Lys Glu Tyr Lys Cys Lys Val
            325                 330                 335

Ser Asn Lys Gly Leu Pro Ser Ser Ile Glu Lys Thr Ile Ser Lys Ala
            340                 345                 350

Lys Gly Gln Pro Arg Glu Pro Gln Val Tyr Thr Leu Pro Pro Ser Gln
        355                 360                 365

Glu Glu Met Thr Lys Asn Gln Val Ser Leu Thr Cys Leu Val Lys Gly
        370                 375                 380

Phe Tyr Pro Ser Asp Ile Ala Val Glu Trp Ser Asn Gly Gln Pro
385                 390                 395                 400

Glu Asn Asn Tyr Lys Thr Thr Pro Pro Val Leu Asp Ser Asp Gly Ser
                405                 410                 415

Phe Phe Leu Tyr Ser Arg Leu Thr Val Asp Lys Ser Arg Trp Gln Glu
```

-continued

```
            420                 425                 430
Gly Asn Val Phe Ser Cys Ser Val Met His Glu Ala Leu His Asn His
                435                 440                 445

Tyr Thr Gln Lys Ser Leu Ser Leu Ser Leu Gly Lys
450                 455                 460
```